(12) United States Patent
Li et al.

(10) Patent No.: US 7,056,925 B2
(45) Date of Patent: Jun. 6, 2006

(54) UREA KINASE INHIBITORS

(75) Inventors: Gaoquan Li, Park City, IL (US); Qun Li, Libertyville, IL (US); Tongmei Li, Waukegan, IL (US); Nan-Horng Lin, Vernon Hills, IL (US); Robert A. Mantei, Franklin, WI (US); Hing L. Sham, Vernon Hills, IL (US); Gary T. Wang, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 215 days.

(21) Appl. No.: 10/640,615

(22) Filed: Aug. 13, 2003

(65) Prior Publication Data

US 2004/0259885 A1 Dec. 23, 2004

Related U.S. Application Data

(60) Provisional application No. 60/403,080, filed on Aug. 13, 2002.

(51) Int. Cl.
*A61K 31/4965* (2006.01)
*C07D 241/00* (2006.01)
*C07D 241/02* (2006.01)
*C07D 211/90* (2006.01)
*C07D 211/78* (2006.01)

(52) U.S. Cl. .............. 514/255.06; 544/336; 544/408; 544/409; 546/286; 546/289; 546/306

(58) Field of Classification Search .............. 544/336, 544/408, 409; 546/286, 289, 306; 514/255.06, 514/349, 353
See application file for complete search history.

(56) References Cited

U.S. PATENT DOCUMENTS

| | | | |
|---|---|---|---|
| 4,405,644 A | 9/1983 | Kabbe et al. | 424/322 |
| 5,547,966 A | 8/1996 | Atwal et al. | 514/352 |
| 2003/0069284 A1* | 4/2003 | Keegan et al. | 514/345 |
| 2004/0014765 A1* | 1/2004 | Boyle et al. | 514/252.02 |

FOREIGN PATENT DOCUMENTS

| | | |
|---|---|---|
| WO | 96/11930 | 4/1996 |
| WO | 96/23769 | 8/1996 |
| WO | 98/50346 | 11/1998 |
| WO | 99/32436 | 7/1999 |
| WO | 00/42012 | 7/2000 |
| WO | 01/04115 | 1/2001 |
| WO | 01/57008 | 8/2001 |
| WO | 01/68568 | 9/2001 |
| WO | 02/070494 | 9/2002 |

\* cited by examiner

*Primary Examiner*—James O. Wilson
*Assistant Examiner*—Zachary C. Tucker
(74) *Attorney, Agent, or Firm*—Johanna M. Corbin; Gregory W. Steele

(57) ABSTRACT

Compounds having the formula

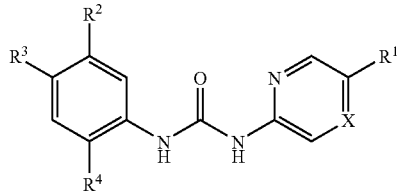

are useful for inhibiting protein kinases. Also disclosed are methods of making the compounds, compositions containing the compounds, and methods of treatment using the compounds.

20 Claims, No Drawings

UREA KINASE INHIBITORS

This application claims priority to U.S. Provisional Patent Application Ser. No. 60/403,080, filed Aug. 13, 2002.

TECHNICAL FIELD

The present invention relates to substituted ureas which are useful for inhibiting protein kinases, methods of making the compounds, compositions containing the compounds, and methods of treatment using the compounds.

BACKGROUND OF THE INVENTION

Protein kinases have been clearly shown to be important in the progression of many disease states that are induced by the inappropriate proliferation of cells. These kinases are often found to be up-regulated in many hyperproliferative states such as cancer. These kinases may be important in cell signaling, where their inappropriate activation induces cells to proliferate (e.g., EGFR, ERBB2, VEGFR, FGFR, PDGFR, c-Met, IGF-1R, RET, TIE2). Alternatively, they may be involved in signal transduction within cells (e.g., c-Src, PKC, Akt, PKA, c-Abl, PDK-1). Often these signal transduction genes are recognized proto-oncogenes. Many of these kinases control cell cycle progression near the G1-S transition (e.g., Cdk2, Cdk4), at the G2-M transition (e.g., Wee1, Myt1, Chk1, Cdc2) or at the spindle checkpoint (Plk, Aurora1 or 2, Bub1 or 3). Furthermore, kinases are intimately linked to the DNA damage response (e.g., ATM, ATR, Chk1, Chk2). Deregulation of these cellular functions: cell signaling, signal transduction, cell cycle control, and DNA repair, are all hallmarks of hyperproliferative diseases, particularly cancer. It is therefore likely that pharmacological modulation of one or more kinases would be useful in slowing or stopping disease progression in these diseases.

SUMMARY OF THE INVENTION

In its principle embodiment, the present invention provides a compound of formula (I)

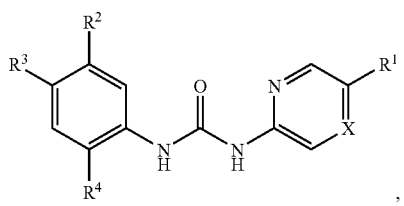

or a therapeutically acceptable salt thereof, wherein

X is —N— or —CH—;

$R^1$ is selected from the group consisting of hydrogen, alkoxy, alkyl, amino, carboxy, cyano, halo, hydroxy, and hydroxyalkyl;

$R^2$ is selected from the group consisting of alkoxy, alkyl, alkylcarbonyl, amino, cyano, halo, and nitro;

$R^3$ is selected from the group consisting of hydrogen, alkoxy, alkyl, amino, aminoalkyl, aminocarbonyl, arylalkyl, cyano, nitro, —$CO_2R^5$, —$COR^5$, and —$SR^5$;

$R^4$ is selected from the group consisting of —$(CHR^6)_mOR^7$, and —$(CH_2)_nNR^8R^9$;

$R^5$ is selected from the group consisting of hydrogen, alkenyl, alkyl, aryl, arylalkyl, cycloalkyl, and (cycloalkyl)alkyl;

$R^6$ is selected from the group consisting of hydrogen, alkyl, aryl, and heteroaryl;

$R^7$ is selected from the group consisting of hydrogen, alkenyl, alkoxyalkoxyalkyl, alkoxyalkyl, alkoxycarbonylalkyl, alkylsulfanylalkyl, alkynyl, aminoalkyl, arylalkyl, arylcarbonylalkyl, aryloxyalkyl, arylsulfanylalkyl, cycloalkenyl, (cycloalkenyl)alkyl, cycloalkyl, (cycloalkyl)alkyl, heteroarylalkoxyalkyl, heteroarylalkyl, (heterocyclyl)alkoxyalkyl, (heterocyclyl)alkyl, and hydroxyalkyl;

$R^8$ and $R^9$ are independently selected from the group consisting of hydrogen, alkenyl, alkoxyalkyl, alkyl, alkylsulfanylalkyl, alkynyl, aminoalkyl, arylalkyl, cycloalkenyl, (cycloalkenyl)alkyl, cycloalkyl, (cycloalkyl)alkyl, heteroarylalkyl, (heterocyclyl)alkyl, and hydroxyalkyl;

m is 0–6; provided that when $R^7$ is hydrogen m is other than 0; and n is 0–6; provided that when $R^8$ and $R^9$ are both hydrogen, n is other than 0.

In a preferred embodiment of compounds of formula (I) are compounds wherein X is —N—.

In another preferred embodiment of compounds of formula (I) are compounds wherein $R^4$ is —$(CH_2)_nNR^8R^9$;

n is 0; and one of $R^8$ and $R^9$ is alkoxyalkyl and the other is selected from the group consisting of alkoxyalkyl and alkyl.

Compounds which support this embodiment include, but are not limited to,

N-{2-[bis(2-methoxyethyl)amino]-5-bromophenyl}-N'-(5-cyano-2-pyrazinyl)urea;

N-{5-bromo-2-[ethyl(2-methoxyethyl)amino]phenyl}-N'-(5-cyano-2-pyrazinyl)urea;

N-{2-[bis(2-methoxyethyl)amino]-5-chlorophenyl}-N'-(5-cyano-2-pyrazinyl)urea;

N-{5-chloro-2-[ethyl(2-methoxyethyl)amino]phenyl}-N'-(5-cyano-2-pyrazinyl)urea; and N-{2-[bis(2-methoxyethyl)amino]-5-cyanophenyl}-N'-(5-cyano-2-pyrazinyl)urea.

In another preferred embodiment of compounds of formula (I) are compounds wherein $R^4$ is —$(CH_2)_nNR^8R^9$;

n is 0; and one of $R^8$ and $R^9$ is arylalkyl and the other is selected from the group consisting of alkyl and hydroxyalkyl.

Compounds which support this embodiment include, but are not limited to,

N-{2-[benzyl(2-hydroxyethyl)amino]-5-bromophenyl}-N'-(5-cyano-2-pyrazinyl)urea;

N-{5-bromo-2-[(2-hydroxy-2-phenylethyl)(methyl)amino]phenyl}-N'-(5-cyano-2-pyrazinyl)urea;

N-{2-[benzyl(2-hydroxyethyl)amino]-5-chlorophenyl}-N'-(5-cyano-2-pyrazinyl)urea;

N-{5-chloro-2-[(2-hydroxy-2-phenylethyl)(methyl)amino]phenyl}-N'-(5-cyano-2-pyrazinyl)urea; and N-{5-cyano-2-[(2-hydroxy-2-phenylethyl)(methyl)amino]phenyl}-N'-(5-cyano-2-pyrazinyl)urea.

In another preferred embodiment of compounds of formula (I) are compounds wherein $R^4$ is —$(CHR^6)_mOR^7$;

m is 0; and $R^7$ is selected from the group consisting of alkoxyalkyl and alkylsulfanylalkyl.

Compounds which support this embodiment include, but are not limited to,

N-[5-chloro-2-(2-methoxy-1-methylethoxy)phenyl]-N'-(5-cyano-2-pyrazinyl)urea;
N-[5-chloro-2-(2-ethoxy-1-methylethoxy)phenyl]-N'-(5-cyano-2-pyrazinyl)urea;
N-[5-chloro-2-(2-methoxyethoxy)phenyl]-N'-(5-cyano-2-pyrazinyl)urea;
N-[5-chloro-2-(2-isopropoxyethoxy)phenyl]-N'-(5-cyano-2-pyrazinyl)urea;
N-[5-chloro-2-(2-ethoxyethoxy)phenyl]-N'-(5-cyano-2-pyrazinyl)urea;
N-{5-chloro-2-[2-(methylsulfanyl)ethoxy]phenyl}-N'-(5-cyano-2-pyrazinyl)urea; and
N-[5-chloro-2-(3-methoxy-3-methylbutoxy)phenyl]-N'-(5-cyano-2-pyrazinyl)urea.

In another preferred embodiment of compounds of formula (I) are compounds wherein
$R^4$ is —$(CHR^6)_m OR^7$;
m is 0; and
$R^7$ is aminoalkyl.

Compounds which support this embodiment include, but are not limited to,
N-(5-chloro-2-{2-[ethyl(3-methylphenyl)amino]ethoxy}phenyl)-N'-(5-cyano-2-pyrazinyl)urea;
N-[2-(3-aminopropoxy)-5-chlorophenyl]-N'-(5-cyano-2-pyrazinyl)urea;
N-{5-chloro-2-[3-(dimethylamino)propoxy]phenyl}-N'-(5-cyano-2-pyrazinyl)urea;
N-{5-chloro-2-[2-(dimethylamino)-1-methylethoxy]phenyl}-N'-(5-cyano-2-pyrazinyl)urea; and
N-(5-chloro-2-{2-[(2-cyanoethyl)(phenyl)amino]ethoxy}phenyl)-N'-(5-cyano-2-pyrazinyl)urea.

In another preferred embodiment of compounds of formula (I) are compounds wherein
$R^4$ is —$(CHR^6)_m OR^7$;
m is 0; and
$R^7$ is (cycloalkyl)alkyl.

Compounds which support this embodiment include, but are not limited to,
N-{5-chloro-2-[(2-methylcyclopropyl)methoxy]phenyl}-N'-(5-cyano-2-pyrazinyl)urea;
N-[5-chloro-2-(cyclopropylmethoxy)phenyl]-N'-(5-cyano-2-pyrazinyl)urea;
N-{5-chloro-2-[(1-methylcyclopropyl)methoxy]phenyl}-N'-(5-cyano-2-pyrazinyl)urea;
N-[5-chloro-2-(2-cyclohexylethoxy)phenyl)-N'-(5-cyano-2-pyrazinyl)urea;
N-{2-[(1S,4S)-bicyclo[2.2.1]hept-2-ylmethoxy]-5-chlorophenyl}-N'-(5-cyano-2-pyrazinyl)urea; and
ethyl 2-{[4-chloro-2-({[(5-cyano-2-pyrazinyl)amino]carbonyl}amino)phenoxy]methyl}cyclopropanecarboxylate.

In another preferred embodiment of compounds of formula (I) are compounds wherein
$R^4$ is —$(CHR^6)_m OR^7$;
m is 0; and
$R^7$ is selected from the group consisting of alkenyl, alkoxyalkoxyalkyl, alkynyl, haloalkyl, and hydroxyalkyl.

Compounds which support this embodiment include, but are not limited to,
N-(5-chloro-2-{[(2S)-2,3-dihydroxypropyl]oxy}phenyl)-N'-(5-cyano-2-pyrazinyl)urea;
N-(5-chloro-2-{[(2R)-2,3-dihydroxypropyl]oxy}phenyl)-N'-(5-cyano-2-pyrazinyl)urea;
N-{5-chloro-2-[2-(2-methoxyethoxy)ethoxy]phenyl}-N'-(5-cyano-2-pyrazinyl)urea;
N-[2-(allyloxy)-5-chlorophenyl]-N'-(5-cyano-2-pyrazinyl)urea;
N-{5-chloro-2-[(3-methyl-2-butenyl)oxy]phenyl}-N'-(5-cyano-2-pyrazinyl)urea;
N-[5-chloro-2-(3-pentynyloxy)phenyl]-N'-(5-cyano-2-pyrazinyl)urea; and
N-[5-chloro-2-(2-chloro-1-methoxyethoxy)phenyl]-N'-(5-cyano-2-pyrazinyl)urea.

In another preferred embodiment of compounds of formula (I) are compounds wherein
$R^4$ is —$(CHR^6)_m OR^7$;
m is 0; and
$R^7$ is selected from the group consisting of alkoxycarbonylalkyl, arylcarbonylalkyl, aryloxyalkyl, cycloalkenyl, cycloalkyl, and heteroarylalkoxyalkyl.

Compounds which support this embodiment include, but are not limited to,
N-[5-chloro-2-(2-cyclohexen-1-yloxy)phenyl]-N'-(5-cyano-2-pyrazinyl)urea;
N-{2-[2-(4-bromophenoxy)ethoxy]-5-chlorophenyl}-N'-(5-cyano-2-pyrazinyl)urea;
N-(5-chloro-2-{2-[3-(6-methyl-2-pyridinyl)propoxy]ethoxy}phenyl)-N'-(5-cyano-2-pyrazinyl)urea;
N-[5-chloro-2-(2-oxo-2-phenylethoxy)phenyl]-N'-(5-cyano-2-pyrazinyl)urea;
N-[5-chloro-2-(3-cyclopenten-1-yloxy)phenyl]-N'-(5-cyano-2-pyrazinyl)urea;
N-(5-chloro-2-{[(3R,4S)-3,4-dihydroxycyclopentyl]oxy}phenyl)-N'-(5-cyano-2-pyrazinyl)urea;
N-(5-chloro-2-{[(1S,3R)-3-hydroxycyclopentyl]oxy}phenyl)-N'-(5-cyano-2-pyrazinyl)urea; and
ethyl 6-[4-chloro-2-({[(5-cyano-2-pyrazinyl)amino]carbonyl}amino)phenoxy]hexanoate.

In another preferred embodiment of compounds of formula (I) are compounds wherein
X is —N—;
$R^1$ is cyano;
$R^2$ is selected from the group consisting of cyano and halo; and
$R^3$ is hydrogen.

In another embodiment, the present invention provides a pharmaceutical composition comprising a compound of formula (I) or a therapeutically acceptable salt thereof, in combination with a therapeutically acceptable carrier.

In another embodiment, the present invention provides a method for inhibiting protein kinases in a patient in recognized need of such treatment comprising administering to the patient a therapeutically acceptable amount of a compound of formula (I), or a therapeutically acceptable salt thereof.

In another embodiment, the present invention provides a method for treating cancer in a patient in recognized need of such treatment comprising administering to the patient a therapeutically acceptable amount of a compound of formula (I), or a therapeutically acceptable salt thereof.

DETAILED DESCRIPTION OF THE INVENTION

As used in the present specification the following terms have the meanings indicated:

The term "alkenyl," as used herein, refers to a straight or branched chain group of two to six carbon atoms containing at least one carbon-carbon double bond.

The term "alkoxy," as used herein, represents an alkyl group attached to the parent molecular moiety through an oxygen atom.

The term "alkoxyalkoxy," as used herein, refers to an alkoxyalkyl group attached to the parent molecular moiety through an oxygen atom.

The term "alkoxyalkyl," as used herein, refers to an alkoxy group attached to the parent molecular moiety through an alkyl group. The alkyl part of the alkoxyalkyl can be optionally substituted with one or two halogen atoms.

The term "alkoxyalkoxyalkyl," as used herein, refers to an alkoxyalkoxy group attached to the parent molecular group through an alkyl group.

The term "alkoxycarbonyl," as used herein, refers to an alkoxy group attached to the parent molecular moiety through a carbonyl group.

The term "alkoxycarbonylalkyl," as used herein, refers to an alkoxycarbonyl group attached to the parent molecular moiety through an alkyl group.

The term "alkyl," as used herein, refers to a group derived from a straight or branched chain saturated hydrocarbon of one to six atoms.

The term "alkylcarbonyl," as used herein, refers to an alkyl group attached to the parent molecular moiety through a carbonyl group.

The term "alkylsulfanyl," as used herein, refers to an alkyl group attached to the parent molecular moiety through a sulfur atom.

The term "alkylsulfanylalkyl," as used herein, refers to an alkylsulfanyl group attached to the parent molecular moiety through an alkyl group.

The term "alkynyl," as used herein, refers to a straight or branched chain group of two to six carbon atoms containing at least one carbon-carbon triple bond.

The term "amino," as used herein, refers to —NR$^a$R$^b$, wherein R$^a$ and R$^b$ are independently selected from the group consisting of hydrogen, alkenyl, alkoxycarbonyl, alkyl, alkylcarbonyl, aryl, arylalkyl, arylcarbonyl, cyanoalkyl, cycloalkyl, (cycloalkyl)alkyl, and nitroalkyl; wherein the aryl and the aryl part of the arylalkyl and the arylcarbonyl can be optionally substituted with one, two, three, four, or five substituents independently selected from the group consisting of alkenyl, alkoxy, alkyl, alkylsulfanyl, cyano, halo, hydroxy, and nitro.

The term "aminoalkyl," as used herein, refers to an amino group attached to the parent molecular moiety through an alkyl group.

The term "aminocarbonyl," as used herein, refers to an amino group attached to the parent molecular moiety through a carbonyl group.

The term "aryl," as used herein, refers to a phenyl group, or a bicyclic or tricyclic fused ring system wherein one or more of the fused rings is a phenyl group. Bicyclic fused ring systems are exemplified by a phenyl group fused to a monocyclic cycloalkenyl group, as defined herein, a monocyclic cycloalkyl group, as defined herein, or another phenyl group. Tricyclic fused ring systems are exemplified by a bicyclic fused ring system fused to a monocyclic cycloalkenyl group, as defined herein, a monocyclic cycloalkyl group, as defined herein, or another phenyl group. Representative examples of aryl include, but are not limited to, anthracenyl, azulenyl, fluorenyl, indanyl, indenyl, naphthyl, phenyl, and tetrahydronaphthyl. The aryl groups of the present invention can be optionally substituted with one, two, three, four, or five substituents independently selected from the group consisting of alkenyl, alkoxy, alkoxyalkyl, alkoxycarbonyl, alkyl, alkylsulfanyl, alkylsulfanylalkyl, amino, aminoalkyl, carboxy, cyano, cyanoalkyl, halo, haloalkoxy, haloalkyl, hydroxy, hydroxyalkyl, nitro, nitroalkyl, and oxo.

The term "arylalkyl," as used herein, refers to an aryl group attached to the parent molecular moiety through an alkyl group. The alkyl part of the arylalkyl can be optionally substituted with one or two substituents independently selected from the group consisting of aryl and hydroxy.

The term "arylcarbonyl," as used herein, refers to an aryl group attached to the parent molecular moiety through a carbonyl group.

The term "arylcarbonylalkyl," as used herein, refers to an arylcarbonyl group attached to the parent molecular moiety through an alkyl group.

The term "aryloxy," as used herein, refers to an aryl group attached to the parent molecular moiety through an oxygen atom.

The term "aryloxyalkyl," as used herein, refers to an aryloxy group attached to the parent molecular moiety through an alkyl group.

The term "arylsulfanyl," as used herein, refers to an aryl group attached to the parent molecular moiety through a sulfur atom.

The term "arylsulfanylalkyl," as used herein, refers to an arylsulfanyl group attached to the parent molecular moiety through an alkyl group.

The term "carbonyl," as used herein, refers to —C(O)—.

The term "carboxy," as used herein, refers to —CO$_2$H.

The term "cyano," as used herein, refers to —CN.

The term "cyanoalkyl," as used herein, refers to a cyano group attached to the parent molecular moiety through an alkyl group.

The term "cycloalkenyl," as used herein, refers to a non-aromatic cyclic or bicyclic ring system having three to ten carbon atoms and one to three rings, wherein each five-membered ring has one double bond, each six-membered ring has one or two double bonds, each seven- and eight-membered ring has one to three double bonds, and each nine-to ten-membered ring has one to four double bonds. Examples of cycloalkenyl groups include cyclohexenyl, octahydronaphthalenyl, norbornylenyl, and the like. The cycloalkenyl groups of the present invention can be optionally substituted with one, two, three, four, or five substituents independently selected from the group consisting of alkenyl, alkoxy, alkoxyalkyl, alkoxycarbonyl, alkyl, alkylsulfanyl, alkylsulfanylalkyl, amino, aminoalkyl, carboxy, cyano, cyanoalkyl, halo, haloalkoxy, haloalkyl, hydroxy, hydroxyalkyl, nitro, nitroalkyl, and oxo.

The term "(cycloalkenyl)alkyl," as used herein, refers to a cycloalkenyl group attached to the parent molecular moiety through an alkyl group.

The term "cycloalkyl," as used herein, refers to a saturated monocyclic, bicyclic, or tricyclic hydrocarbon ring system having three to twelve carbon atoms. Examples of cycloalkyl groups include cyclopropyl, cyclopentyl, bicyclo [3.1.1]heptyl, adamantyl, and the like. The cycloalkyl groups of the present invention can be optionally substituted with one, two, three, four, or five substituents independently selected from the group consisting of alkenyl, alkoxy, alkoxyalkyl, alkoxycarbonyl, alkyl, alkylsulfanyl, alkylsulfanylalkyl, amino, aminoalkyl, carboxy, cyano, cyanoalkyl, halo, haloalkoxy, haloalkyl, hydroxy, hydroxyalkyl, nitro, nitroalkyl, and oxo.

The term "(cycloalkyl)alkyl," as used herein, refers to a cycloalkyl group attached to the parent molecular moiety through an alkyl group.

The terms "halo," and "halogen," as used herein, refer to F, Cl, Br, and I.

The term "haloalkoxy," as used herein, refers to a haloalkyl group attached to the parent molecular moiety through an oxygen atom.

The term "haloalkyl," as used herein, refers to an alkyl group substituted by one, two, three, or four halogen atoms.

The term "heteroaryl," as used herein, refers to an aromatic five- or six-membered ring where at least one atom is selected from the group consisting of N, O, and S, and the remaining atoms are carbon. The five-membered rings have two double bonds, and the six-membered rings have three double bonds. The heteroaryl groups are connected to the parent molecular group through a substitutable carbon or nitrogen atom in the ring. The term "heteroaryl" also includes bicyclic systems where a heteroaryl ring is fused to a phenyl group, a monocyclic cycloalkenyl group, as defined herein, a monocyclic cycloalkyl group, as defined herein, a heterocyclyl group, as defined herein, or an additional heteroaryl group; and tricyclic systems where a bicyclic system is fused to a phenyl group, a monocyclic cycloalkenyl group, as defined herein, a monocyclic cycloalkyl group, as defined herein, a heterocyclyl group, as defined herein, or an additional heteroaryl group. Heteroaryls are exemplified by benzothienyl, benzoxadiazolyl, cinnolinyl, dibenzofuranyl, furanyl, imidazolyl, indazolyl, indolyl, isoxazolyl, isoquinolinyl, isothiazolyl, naphthyridinyl, oxadiazolyl, oxadiazolyl, oxazolyl, thiazolyl, thienopyridinyl, thienyl, triazolyl, thiadiazolyl, pyridinyl, pyridazinyl, pyrimidinyl, pyrazinyl, pyrazolyl, pyrrolyl, quinolinyl, triazinyl, and the like. The heteroaryl groups of the present invention can be optionally substituted with one, two, three, four, or five substituents independently selected from the group consisting of alkenyl, alkoxy, alkoxyalkyl, alkoxycarbonyl, alkyl, alkylsulfanyl, alkylsulfanylalkyl, amino, aminoalkyl, carboxy, cyano, cyanoalkyl, halo, haloalkoxy, haloalkyl, hydroxy, hydroxyalkyl, nitro, nitroalkyl, and oxo.

The term "heteroarylalkoxy," as used herein, refers to a heteroarylalkyl group attached to the parent molecular moiety through an oxygen atom.

The term "heteroarylalkoxyalkyl," as used herein, refers to a heteroarylalkoxy group attached to the parent molecular moiety through an alkyl group.

The term "heteroarylalkyl," as used herein, refers to a heteroaryl group attached to the parent molecular moiety through an alkyl group. The alkyl part of the heteroaryl can be optionally substituted with one or two hydroxy groups.

The term "heterocyclyl," as used herein, refers to cyclic, non-aromatic, five-, six-, or seven-membered rings containing at least one atom selected from the group consisting of oxygen, nitrogen, and sulfur. The five-membered rings have zero or one double bonds and the six- and seven-membered rings have zero, one, or two double bonds. The heterocyclyl groups of the invention are connected to the parent molecular group through a substitutable carbon or nitrogen atom in the ring. The term "heterocyclyl" also includes bicyclic systems where a heterocyclyl ring is fused to a phenyl group, a monocyclic cycloalkenyl group, as defined herein, a monocyclic cycloalkyl group, as defined herein, or an additional monocyclic heterocyclyl group; and tricyclic systems where a bicyclic system is fused to a phenyl group, a monocyclic cycloalkenyl group, as defined herein, a monocyclic cycloalkyl group, as defined herein, or an additional monocyclic heterocyclyl group. Heterocyclyl groups of the invention are exemplified by benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocyclyl groups of the present invention can be optionally substituted with one, two, three, four, or five substituents independently selected from the group consisting of alkenyl, alkoxy, alkoxyalkyl, alkoxycarbonyl, alkyl, alkylsulfanyl, alkylsulfanylalkyl, amino, aminoalkyl, carboxy, cyano, cyanoalkyl, halo, haloalkoxy, haloalkyl, hydroxy, hydroxyalkyl, nitro, nitroalkyl, and oxo.

The term "(heterocyclyl)alkoxy," as used herein, refers to a (heterocyclyl)alkyl group attached to the parent molecular moiety through an oxygen atom.

The term "(heterocyclyl)alkoxyalkyl," as used herein, refers to a (heterocyclyl)alkoxy group attached to the parent molecular moiety through an alkyl group.

The term "(heterocyclyl)alkyl" as used herein, refers to a heterocyclyl group attached to the parent molecular moiety through an alkyl group. The alkyl part of the (heterocyclyl)alkyl can be optionally substituted with one or two hydroxy groups.

The term "hydroxy," as used herein, refers to —OH.

The term "hydroxyalkyl," as used herein, refers to a hydroxy group attached to the parent molecular moiety through an alkyl group. The alkyl part of the hydroxyalkyl can be optionally substituted with an additional hydroxy group.

The term "nitro," as used herein, refers to —NO$_2$.

The term "nitroalkyl," as used herein, refers to a nitro group attached to the parent molecular moiety through an alkyl group.

The term "oxo," as used herein, refers to =O.

The compounds of the present invention can exist as therapeutically acceptable salts. The term "therapeutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate, lactate, maleate, mesitylenesulfonate, methanesulfonate, naphthylenesulfonate, nicotinate, 2-naphthalenesulfonate, oxalate, pamoate, pectinate, persulfate, 3-phenylproprionate, piorate, pivalate, propionate, succinate, tartrate, trichloroacetate,trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to parent compounds of formula (I) for example, by hydrolysis in blood.

Asymmetric centers exist in the compounds of the present invention. These centers are designated by the symbols "R" or "S," depending on the configuration of substituents around the chiral carbon atom. It should be understood that the invention encompasses all stereochemical isomeric forms, or mixtures thereof, which possess the ability to inhibit protein kinases. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

In accordance with methods of treatment and pharmaceutical compositions of the invention, the compounds can be administered alone or in combination with other anticancer agents. When using the compounds, the specific therapeutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used. The compounds can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrasternal injection.

Parenterally administered aqueous or oleaginous suspensions of the compounds can be formulated with dispersing, wetting, or suspending agents. The injectable preparation can also be an injectable solution or suspension in a diluent or solvent. Among the acceptable diluents or solvents employed are water, saline, Ringer's solution, buffers, monoglycerides, diglycerides, fatty acids such as oleic acid, and fixed oils such as monoglycerides or diglycerides.

The inhibitory effect of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches can also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents, and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes therefore.

Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds with a suitable non-irritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of this invention.

The total daily dose of the compounds administered to a host in single or divided doses can be in amounts from about 0.1 to about 200 mg/kg body weight or preferably from about 0.25 to about 100 mg/kg body weight. Single dose compositions can contain these amounts or submultiples thereof to make up the daily dose.

Determination of Biological Activity

The Chk1 enzymatic assay was carried out using recombinant Chk1 kinase domain protein covering amino acids from residue 1 to 289 and a polyhistidine tag at the C-terminal end. Human cdc25c peptide substrate contained a sequence from amino acid residue 204 to 225. The reaction mixture contained 25 mM of HEPES at pH 7.4, 10 mM $MgCl_2$, 0.08 mM Triton X-100, 0.5 mM DTT, 5 µM ATP, 4 nM 33P ATP, 5 µM cdc25c peptide substrate, and 6.3 nM of the recombinant Chk1 protein. Compound vehicle DMSO was maintained at 2% in the final reaction. After 30 minutes at room temperature, the reaction was stopped by addition of equal volume of 4M NaCl and 0.1M EDTA, pH 8. A 40 µL aliquot of the reaction was added to a well in a Flash Plate (NEN Life Science Products, Boston, Mass.) containing 160 µL of phosphate-buffered saline (PBS) without calcium chloride and magnesium chloride and incubated at room temperature for 10 minutes. The plate was then washed 3 times in PBS with 0.05% of Tween-20 and counted in a Packard TopCount counter (Packard BioScience Company, Meriden, Conn.).

Compounds of the present invention inhibited Chk1 at $IC_{50}$ values between about 2 nM and about 5 µM. Preferred compounds inhibited Chk1 at $IC_{50}$ values between about 2 nM and about 200 nM. Most preferred compounds inhibited Chk1 at $IC_{50}$ values between about 2 nM and about 40 nM. Thus, the compounds of the invention are useful in treating disorders which are caused or exacerbated by increased protein kinase levels.

The compounds of the invention, including not limited to those specified in the examples, possess the ability to inhibit protein kinases. As protein kinase inhibitors, such compounds are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such compounds may also be useful in treating solid tumors arising from hematopoietic malignancies such as leukemias (i.e., chloromas, plasmacytomas and the plaques and tumors of mycosis fungicides and cutaneous T-cell lymphoma/leukemia) as well as in the treatment of lymphomas (both Hodgkin's and non-Hodgkin's lymphomas). In addition, these compounds may be useful in the prevention of metastases from the tumors described above either when used alone or in combination with radiotherapy and/or other chemotherapeutic agents. The compounds of the invention can also be useful in the treatment of the aforementioned conditions by mechanisms other than the inhibition of angiogenesis.

Synthetic Methods

Abbreviations which have been used in the descriptions of the scheme and the examples that follow are: THF for tetrahydrofuran; MTBE for methyl tert-butyl ether; DIBALH for diisobutylaluminum hydride, and TFA for trifluoroacetic acid.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. The groups X, $R^1$, $R^2$, $R^3$, $R^4$, $R^5$, $R^6$, $R^7$, $R^8$, $R^9$, m, and n are as defined above unless otherwise noted below.

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

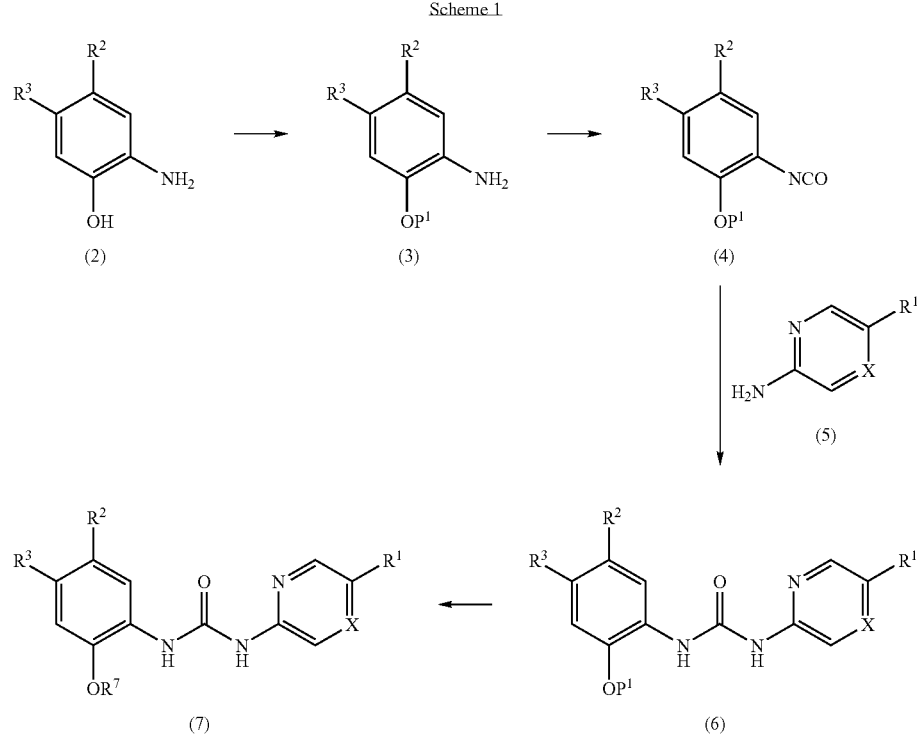

Scheme 1

As shown in Scheme 1, compounds of formula (2) can be converted to compounds of formula (3) ($P^1$ is a hydroxy protecting group such as a trialkylsilyl group) can be prepared by methods known to those of ordinary skill in the art (i.e., treatment with the appropriate protecting reagent in the presence of a base). Compounds of formula (3) can be treated with triphosgene in the presence of a base such as triethylamine or diisopropylethylamine to provide compounds of formula (4). Examples of solvents used in this reaction include dichloromethane, carbon tetrachloride, and chloroform. The reaction is typically run at about −10° C. to about 10° C. for about 1 to about 6 hours.

Compounds of formula (6) can be prepared by reacting compounds of formula (4) with compounds of formula (5). Examples of solvents used in these reactions include toluene, xylene, and mesitylene. The reaction is typically conducted at about 90° C. to about 120° C. for about 24 to about 62 hours. Compounds of formula (6) can be converted to the corresponding alcohol (using deprotection conditions known to those of ordinary skill in the art) and then subsequently treated with an appropriately substituted alcohol ($R^7OH$) in the presence of a trialkyl or triarylphosphine (such as tributylphosphine or triphenylphosphine) and a coupling reagent such as di-tert-butyl azodicarboxylate, diisopropyl azodicarboxylate, or diethyl azodicarboxylate to provide compounds of formula (7) (compounds of formula (I) where $R^4$ is —$CH(R^6)_mOR^7$ and m is 0). Examples of solvents used in this reaction include THF, MTBE, and diethyl ether. The reaction is typically conducted at about 20° C. to about 30° C. for about 8 to about 24 hours.

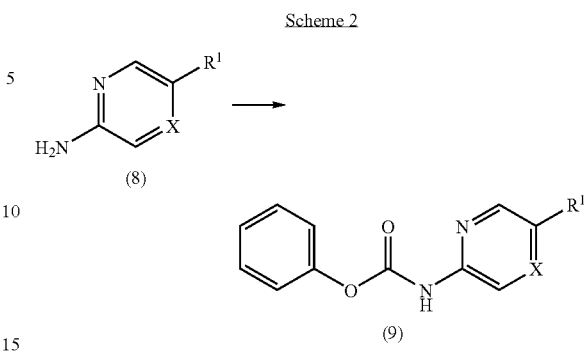

Scheme 2 shows the conversion of compounds of formula (8) to compounds of formula (9). The $R^1$ group of compounds of formula (8) can be added to the corresponding unsubstituted heterocyclic amine by aromatic halogenation followed by conversion of the halogen to the desired functional group using methods known to those of ordinary skill in the art. Treatment of compounds of formula (8) with phenyl chloroformate in the presence of a base such as pyridine, triethylamine, or diisopropylethylamine provides compounds of formula (9). Examples of solvents used in this reaction include dichloromethane, THF, and mixtures thereof. The reaction is typically conducted at about 15° C. to about 35° C. for about 8 to about 24 hours.

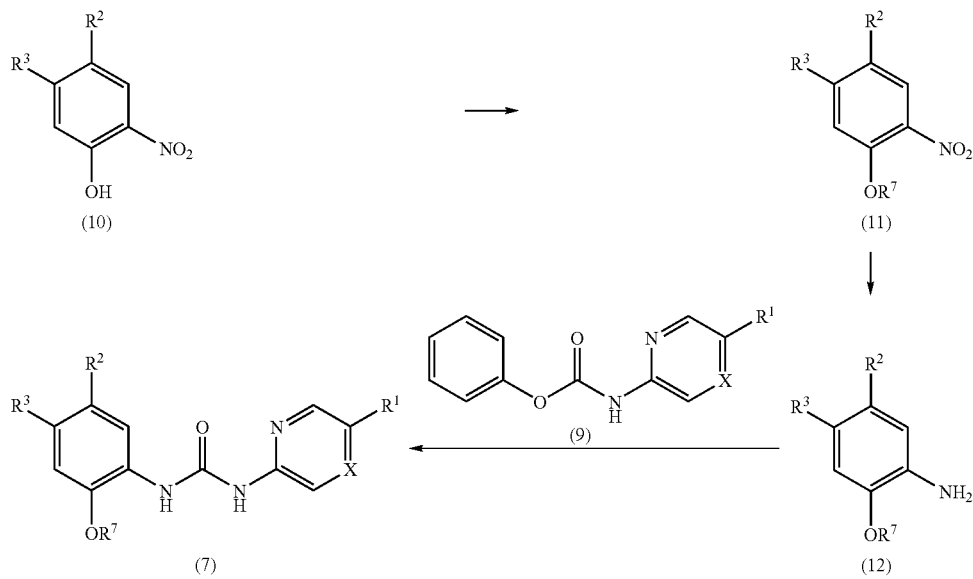

Scheme 3 shows an alternative synthesis of compounds of formula (7). Compounds of formula (10) can be converted to compounds of formula (11) following the procedures described in Scheme 1. Reduction of compounds of formula (11) to compounds of formula (12) can be accomplished by treatment with a reducing agent such as hydrogen and Raney nickel; hydrogen and platinum oxide; or hydrogen and catalytic ruthenium. Examples of solvents used in this reaction include water, methanol, ethanol, and mixtures thereof. The reaction is typically conducted at about 25° C. to about 60° C. for about 15 minutes to about 4 hours.

Compounds of formula (7) can be prepared from compounds of formula (12) by treatment with compounds of formula (9) (prepared according to the procedure described in Scheme 2). Examples of solvents used in this reaction include toluene, xylene, and mesitylene. The reaction is typically conducted at about 100° C. to about 120° C. for about 1 to about 6 hours.

Scheme 4

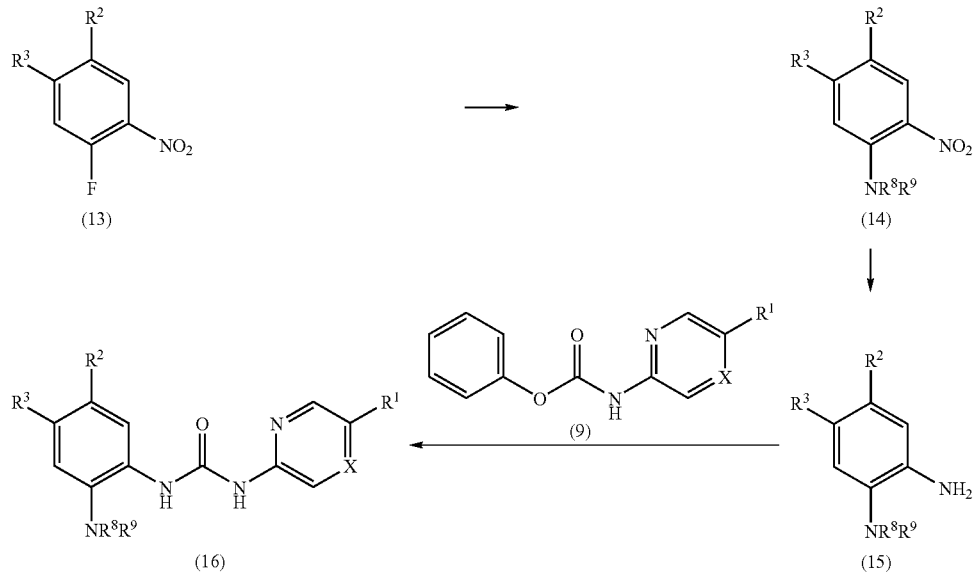

As shown in Scheme 4, compounds of formula (13) can be converted to compounds of formula (14) by treatment with an appropriately substituted amine (HNR$^8$R$^9$). Examples of solvents used in this reaction include acetonitrile, toluene, and benzene. The reaction is typically conducted at a temperature of about 70° C. to about 90° C. for about 8 to about 24 hours. Compounds of formula (14) can be reduced to compounds of formula (15) by the methods described in Scheme 3. Compounds of formula (15) can be reacted with compounds of formula (9) (prepared according to the procedure described in Scheme 2) to provide compounds of formula (16) (compounds of formula (I) where R$^4$ is —(CH$_2$)$_n$NR$^8$R$^9$ and n is 0) using the conditions described in Scheme 3.

Scheme 5 shows the preparation of compounds of formula (19) (compounds of formula (I) where R$^4$ is —(CH$_2$)$_n$NR$^8$R$^9$ and n is 1–6). Compounds of formula (17) (n is 1–6) can be treated with an appropriately substituted amine (HNR$^8$R$^9$) in the presence of a base such as triethylamine or pyridine to provide compounds of formula (18). Conversion of compounds of formula (18) to compounds of formula (19) can be accomplished by the methods described in Scheme 4.

Scheme 5

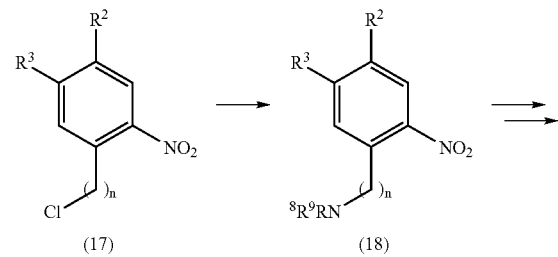

Scheme 6

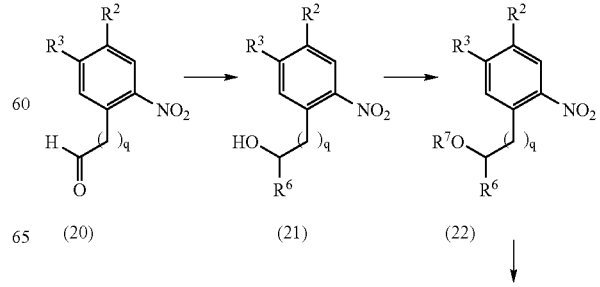

-continued

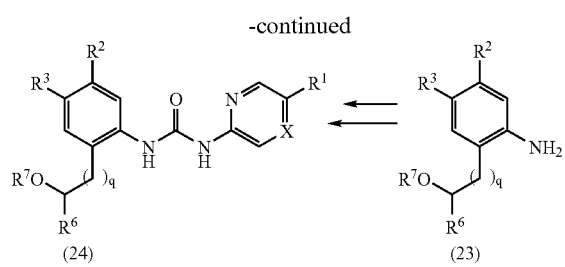

The preparation of compounds of formula (24) (compounds of formula (I) where $R^4$ is —$(CHR^6)_mOR^7$ and m is 1–6) is shown in Scheme 6. Compounds of formula (20) (q is 0–5) can be converted to compounds of formula (21) by treatment with an alkyl-, aryl-, or heteroaryllithium reagent to provide compounds of formula (21) where $R^6$ is alkyl, aryl, or heteroaryl; or by treatment with a reducing agent such as DIBAL-H to provide compounds of formula (21) where $R^6$ is hydrogen. These reactions are typically conducted in solvents such as THF, toluene, and hexanes at temperatures between about −78° C. and about 0° C.

Compounds of formula (21) can be converted to compounds of formula (22) where $R^7$ is other than hydrogen by treatment with an appropriately substituted alcohol and a coupling reagent, as described in Scheme 1.

Reduction of compounds of formula (22) to compounds of formula (23) followed by conversion to compounds of formula (24) (compounds of formula (I) where $R^4$ is —$(CHR^6)_mOR^7$ and m is 1–6) can be accomplished by the methods described in Scheme 1, or, alternatively, by the methods described in Scheme 3.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/ChemSketch version 5.0 (developed by Advanced Chemistry Development, Inc., Toronto, ON, Canada) or were given names which appeared to be consistent with ACD nomenclature.

EXAMPLE 1

N-[5-chloro-2-(2-cyclohexen-1-yloxy)phenyl]-N'-(5-cyano-2-pyrazinyl)urea

EXAMPLE 1A 5-bromo-2-pyrazinamine

A 0° C. solution of 2-aminopyrazine (15.0 g, 157 mmol) in dichloromethane (900 mL) was treated with N-bromosuccinimide (28.2 g, 159 mmol), stirred for 3.5 hours, and filtered through diatomaceous earth (Celite®). The filtrate was treated with silica gel (300 g) and concentrated. The concentrate was purified by flash column chromatography with 30% ethyl acetate/hexanes to provide 22.09 g (81.5%) of the desired product. MS (APCI(+)) m/z 174 (M+H)+; 1H NMR (300 MHz, CDCl3) δ 8.09 (d, J=1.4 Hz, 1H), 7.77 (d, J=1.7 Hz, 1H), 4.30–4.78 (br s, 2H).

EXAMPLE 1B 5-amino-2-pyrazinecarbonitrile

A mixture of Example 1A (19.29 g, 105 mmol), freshly powdered KCN (16.9 g, 260 mmol), CuI (49.5 g, 260 mmol), 18-crown-6 (2.08 g, 7.8 mmol), and (PPh3)4Pd (1.8 g, 1.57 mmol) in N,N-dimethylformamide (600 mL) was stirred at room temperature for 30 minutes and heated to reflux in an oil bath preheated to about 200° C. The solution was stirred at reflux for 3 hours, cooled to room temperature, poured into ethyl acetate (1 L), filtered through diatomaceous earth (Celite®), treated with silica gel (100 g), and concentrated. The concentrate was purified by flash column chromatography on silica gel with 60% ethyl acetate/hexanes to provide 11.9 g (94.4%) of the desired product. MS (APCI(+)) m/z 121 (M+H)+; 1H NMR (300 MHz, DMSO-d6) δ 8.40 (d, J=0.7 Hz, 1H), 7.90 (d, J=0.7 Hz, 1H), 7.47–7.69 (br s, 2H).

EXAMPLE 1C

2-{[tert-butyl(dimethyl)silyl]oxy}-5-chloroaniline

A solution of 2-amino-4-chlorophenol (14.3 g, 100 mmol), tert-butyldimethylsilyl chloride (18 g, 120 mmol) and imidazole (14 g, 200 mmol) in DMF (250 mL) was stirred at room temperature for 24 hours, concentrated, and partitioned between brine (300 mL) and ethyl acetate (300 mL). The aqueous phase was extracted with ethyl acetate. The combined phases were dried (MgSO4), filtered, and concentrated. The concentrate was purified by flash column chromatography on silica gel with 15% ethyl acetate/hexanes to provide 18.5 g (71.7% )of the desired product. MS (DCI/NH3) m/z 258 (M+H)+; 1H NMR (300 MHz, CDCl3) δ 6.70 (d, J=2.71 Hz, 1H), 6.64 (d, J=8.5 Hz, 1H), 6.57 (dd, J=2.7 and 8.5 Hz, 1H), 3.75 (br s, 2H), 1.01 (s, 9H), 0.23 (s, 6H).

EXAMPLE 1D tert-butyl(4-chloro-2-isocyanatophenoxy)dimethylsilane

A 0° C. solution of triphosgene (1.2 g, 4 mmol) in dichloromethane (30 mL) was treated with a solution of Example 1C (2.58 g, 10 mmol) and triethylamine (2.8 mL, 20 mmol) in dichloromethane (15 mL) dropwise over 15 minutes. The mixture was stirred at 0° C. for 3 hours and diluted with dichloromethane (100 mL). The solution was then washed with cold brine (100 mL), dried (MgSO4), filtered, and concentrated. The concentrate was purified by flash column chromatography on silica gel with 5% ethyl acetate/hexanes to provide 2.51 g (89%) of the desired product. $^1$H NMR (300 MHz, CDCl$_3$) δ 6.98–7.03 (m, 2H), 6.78 (d, J=9.2 Hz, 1H), 1.09 (s, 9H), 0.31 (s, 6H).

EXAMPLE 1E

N-(2-{[tert-butyl(dimethyl)silyl]oxy}-5-chlorophenyl)-N'-(5-cyano-2-pyrazinyl)urea A mixture of Example 1B (0.84 g, 7 mmol) and Example 1D (2.0 g, 7.06 mmol) in toluene (20 mL) was heated to reflux for 48 hours, cooled to room temperature, and filtered. The filter cake was washed with hexanes (2×10 mL) to provide 1.66 g (58.5%) of the desired product. MS (ESI(−)) m/z 402 (M−H)$^-$; $^1$H NMR (500 MHz, DMSO-d$_6$) δ 10.99 (s, 1H), 9.33 (s, 1H), 9.00 (d, J=1.3 Hz, 1H), 8.82 (d, J=1.36 Hz, 1H), 8.07 (d, J=2.7 Hz, 1H), 7.07 (dd, J=2.7 and 8.8 Hz, 1H), 6.97 (d, J=2.71 Hz, 1H), 0.98 (s, 9H), 0.32 (s, 6H).

EXAMPLE 1F

N-(5-chloro-2-hydroxyphenyl)-N'-(5-cyano-2-pyrazinyl)urea

A solution of Example 1E (1.66 g, 4.1 mmol) in DMF (25 mL) at room temperature was treated sequentially with 48% wt HBr (0.1 mL) and KF (0.48 g, 8.2 mmol). The mixture was stirred for 30 minutes, poured into 1N aqueous HCl (100 mL), and extracted with ethyl acetate (3×80 mL). The combined extracts were dried (MgSO$_4$), filtered, and concentrated. The concentrate was purified by flash column chromatography on silica gel with 60% ethyl acetate/hexanes to provide 0.97 g (82.2%) of the desired product. MS (ESI(−)) m/z 288 (M−H)$^-$; $^1$H NMR (500 MHz, DMSO-d$_6$) δ 10.69 (br s, 1H), 10.48 (br s, 1H), 9.64 (s, 1H), 9.13 (d, J=1.3 Hz, 1H), 8.86 (d, J=1.3 Hz, 1H), 8.16 (d, J=2.4 Hz, 1H), 6.93 (dd, J=8.5 and 2.4 Hz, 1H), 6.87 (d, J=8.5 Hz, 1H).

EXAMPLE 1G

N-[5-chloro-2-(2-cyclohexen-1-yloxy)phenyl]-N'-(5-cyano-2-pyrazinyl)urea

A mixture of Example 1F (28.9 mg, 0.10 mmol), 2-cyclohexen-1-ol (9.8 mg, 0.10 mmol), di-tert-butylazocarboxylate (34.5 mg, 0.15 mmol), triphenylphosphine on polystyrene (3 mmol/g, 50 mg, 0.15 mmol) and THF (2 mL) in a capped 4-mL vial was shaken at room-temperature overnight and filtered. The resin was washed twice with THF (1 mL each) and the combined THF washes were concentrated. The concentrate was purified by preparative HPLC with acetonitrile/water containing 0.1% TFA to provide 4.4 mg (12%) of the desired product. MS (ESI(−)) m/z 368 (M−H)$^-$; $^1$H NMR (500 MHz, DMSO-d$_6$) δ 10.99 (s, 1H), 10.05 (br s, 1H), 8.92 (s, 1H), 8.73 (s, 1H), 8.27 (d, J=2.5 Hz, 1H), 7.17 (d, J=8.7 Hz, 1H), 7.06 (dd, J=8.9, 2.7 Hz, 1H), 6.01–6.08 (m, 1H), 5.85–5.92 (m, 1H), 4.97–5.04 (m, 1H), 1.89–2.19 (m, 3H), 1.73–1.85 (m, 2H), 1.56–1.68 (m, 1H).

EXAMPLE 2

N-{5-chloro-2-[(2-methylcyclopropyl)methoxy]phenyl}-N'-(5-cyano-2-pyrazinyl)urea The desired product (5.0 mg, 14%) was prepared by substituting (2-methylcyclopropyl)methanol (8.61 mg, 0.10 mmol) for 2-cyclohexen-1-ol in Example 1G. MS (ESI(−)) m/z 356 (M−H)$^-$; $^1$H NMR (500 MHz, DMSO-d$_6$) δ 10.96 (s, 1H), 10.17 (br s, 1H), 8.93 (s, 1H), 8.85 (s, 1H), 8.25 (d, J=2.2 Hz, 1H), 7.07 (d, J=8.4 Hz, 1H), 7.05 (dd, J=8.7, 2.2 Hz, 1H), 4.01 (dd, J=10.6, 6.9 Hz, 1H), 3.94 (dd, J=10.8, 7.0 Hz, 1H), 1.04–1.11 (m, 1H), 1.04 (d, J=5.9 Hz, 3H), 0.73–0.83 (m, 1H), 0.50–0.56 (m, 1H), 0.33–0.40 (m, 1H).

EXAMPLE 3

N-[5-chloro-2-(cyclopropylmethoxy)phenyl]-N'-(5-cyano-2-pyrazinyl)urea

The desired product (3.4 mg, 10%) was prepared substituting cyclopropylmethanol (7.21 mg, 0.10 mmol) for 2-cyclohexen-1-ol in Example 1G. MS (ESI(−)) m/z 343 (M−H)$^-$; $^1$H NMR (500 MHz, DMSO-d$_6$) δ 10.96 (s, 1H), 10.28 (br s, 1H), 8.90 (s, 1H), 8.83 (s, 1H), 8.25–8.27 (m, 1H), 7.05–7.07 (m, 2H), 3.96 (s, 1H), 3.95 (s, 1H), 1.31–1.42 (m, 1H), 0.59–0.67 (m, 2H), 0.33–0.40 (m, 2H).

EXAMPLE 4

N-{5-chloro-2-[(1-methylcyclopropyl)methoxy]phenyl}-N'-(5-cyano-2-pyrazinyl)urea The desired product (3.9 mg, 11%) was prepared by substituting (1-methylcyclopropyl)methanol (8.6 mg, 0.10 mmol) for 2-cyclohexen-1-ol in Example 1G. MS (ESI(−)) m/z 358 (M−H)$^-$; $^1$H NMR (500 MHz, DMSO-d$_6$) δ 11.06 (br s, 1H), 9.98 (br s, 1H), 8.91 (s, 1H), 8.77 (s, 1H), 8.26 (d, J=2.2 Hz, 1H), 7.06 (dd, J=8.7, 2.2 Hz, 1H), 7.03 (d, J=8.7 Hz, 1H), 3.87–3.90 (m, 2H), 1.25 (s, 3H), 0.56–0.60 (m, 2H), 0.46–0.50 (m, 2H).

EXAMPLE 5

N-[5-chloro-2-(2-cyclohexylethoxy)phenyl]-N'-(5-cyano-2-pyrazinyl)urea

The desired product (7.6 mg, 19%) was prepared by substituting 2-cyclohexylethanol (12.8 mg, 0.10 mmol) for 2-cyclohexen-1-ol in Example 1G. MS (ESI(−)) m/z 400 (M−H)$^-$, $^1$H NMR (500 MHz, DMSO-d$_6$) δ 10.96 (s, 1H), 9.94 (br s, 1H), 8.97 (s, 1H), 8.81 (s, 1H), 8.24 (d, J=2.5 Hz, 1H), 7.10 (d, J=8.7 Hz, 1H), 7.06 (dd, J=8.7, 2.5 Hz, 1H), 4.08–4.19 (m, 2H), 1.70–1.80 (m, 4H), 1.63–1.70 (m, 2H), 1.44–1.53 (m, 1H), 1.32–1.43 (m, 1H), 1.10–1.21 (m, 3H), 0.92–1.04 (m, 2H).

EXAMPLE 6

N-{2-[(1S,4S)-bicyclo[2.2.1]hept-2-ylmethoxy]-5-chlorophenyl}-N'-(5-cyano-2-pyrazinyl)urea The desired product (10.3 mg, 26%) was prepared by substituting (1S,4S)-bicyclo[2.2.1]hept-2-ylmethanol (12.6 mg, 0.10 mmol) for 2-cyclohexen-1-ol in Example 1G. MS (ESI(−)) m/z 398 (M−H)$^{31}$; $^1$H NMR (500 MHz, DMSO-d$_6$) δ 11.01 (br s, 1H), 9.80–10.03 (br s, 1H), 8.93–9.00 (m, 1H), 8.77–8.84 (m, 1H), 8.21–8.27 (m, 1H), 7.12–7.17 (m, 1H), 7.05–7.10 (m, 1H), 3.96–4.12 (m, 1H), 3.76–3.90 (m, 1H), 2.34–2.47 (m, 1H), 2.17–2.28 (m, 1H) 1.28–1.56 (m, 8H), 0.70–0.99 (m, 1H).

EXAMPLE 7

N-{2-[2-(4-bromophenoxy)ethoxy]-5-chlorophenyl}-N'-(5-cyano-2-pyrazinyl)urea

The desired product (4.4 mg, 9%) was prepared by substituting 2-(4-bromophenoxy)ethanol (21.71 mg, 0.10 mmol) for 2-cyclohexen-1-ol in Example 1G. MS (ESI(−))

m/z 488 (M−H)⁻; ¹H NMR (500 MHz, DMSO-d₆) δ 10.90 (s, 1H), 10.36 (br s, 1H), 8.80 (s, 1H), 8.56 (s, 1H), 8.27 (d, J=2.8 Hz, 1H), 7.41 (d, J=9.0 Hz, 2H), 7.17 (d, J=8.7 Hz, 1H), 7.10 (dd, J=8.7, 2.5 Hz, 1H), 6.93 (d, J=9.0 Hz, 2H), 4.38–4.49 (m, 4H).

EXAMPLE 8

N-(5-chloro-2-{2-[ethyl(3-methylphenyl)amino]ethoxy}phenyl)-N'-(5-cyano-2-pyrazinyl)urea The desired product (4.9 mg, 11%) was prepared by substituting 2-[ethyl(3-methylphenyl)amino]ethanol (17.83 mg, 0.10 mmol) for 2-cyclohexen-1-ol in Example 1G. MS (ESI(−)) m/z 449 (M−H)⁻; ¹H NMR (500 MHz, DMSO-d₆) δ 10.91 (s, 1H), 10.03 (br s, 1H), 8.93 (s, 1H), 8.77 (s, 1H), 8.23 (d, J=2.5 Hz, 1H), 7.13 (d, J=8.7 Hz, 1H), 7.06 (dd, J=8.7, 2.5 Hz, 1H), 7.00 (m, 1H), 6.51 (m, 2H), 6.40 (m, 1H), 4.26 (t, J=6.1 Hz, 2H), 3.74 (t, J=6.2 Hz, 2H), 3.39 (t, J=10.9 Hz, 2H), 2.19 (s, 3H), 1.04 (t, J=7.0 Hz, 3H).

EXAMPLE 9

N-(5-chloro-2-{[(2S)-2,3-dihydroxypropyl]oxy}phenyl)-N'-(5-cyano-2-pyrazinyl)urea

EXAMPLE 9A

N-(5-chloro-2-{[(4R)-2,2-dimethyl-1,3-dioxolan-4-yl]methoxy}phenyl)-N'-(5-cyano-2-pyrazinyl)urea The desired product was prepared by substituting [(4R)-2,2-dimethyl-1,3-dioxolan-4-yl]methanol (13.2 mg, 0.10 mmol) for 2-cyclohexen-1-ol in Example 1G.

EXAMPLE 9B

N-(5-chloro-2-{[(2S)-2,3-dihydroxypropyl]oxy}phenyl)-N'-(5-cyano-2-pyrazinyl)urea A solution Example 9A in trifluoroacetic acid (0.1 mL) and dichloromethane (0.9 mL) was shaken at room-temperature overnight and concentrated. The concentrate was purified by preparative HPLC with acetonitrile/water containing 0.1% TFA to provide 2.2 mg (6%) of the desired product. MS (ESI(−)) m/z 362 (M−H)⁻; ¹H NMR (500 MHz, DMSO-d₆) δ 10.92 (br s, 1H), 10.41 (br s, 1H), 8.87 (s, 1H), 8.83 (s, 1H), 8.28 (d, J=2.2 Hz, 1H), 7.09 (d, J=8.7 Hz, 1H), 7.07 (dd, J=8.9, 2.0 Hz, 1H), 5.04 (br s, 1H), 4.74 (br s, 1H), 4.11 (dd, J=10.0, 4.1 Hz, 1H), 4.01 (dd, J=9.7, 5.9 Hz, 1H), 3.93 (br s, 1H), 3.53 (br s, 2H).

EXAMPLE 10

N-(5-chloro-2-{[(2R)-2,3-dihydroxypropyl]oxy}phenyl)-N'-(5-cyano-2-pyrazinyl)urea

EXAMPLE 10A

N-(5-chloro-2-{[(4S)-2,2-dimethyl-1,3-dioxolan-4-yl]methoxy}phenyl)-N'-(5-cyano-2-pyrazinyl)urea The desired product was prepared by substituting [(4S)-2,2-dimethyl-1,3-dioxolan-4-yl]methanol (13.2 mg, 0.10 mmol) for 2-cyclohexen-1-ol in Example 1G.

EXAMPLE 10B

N-(5-chloro-2-{[(2R)-2,3-dihydroxypropyl]oxy}phenyl)-N'-(5-cyano-2-pyrazinyl)urea The desired product (2.5 mg, 7%) was prepared by substituting Example 10A for Example 9A in Example 9B. MS (ESI(−)) m/z 362 (M−H)⁻; ¹H NMR (500 MHz, DMSO-d₆) δ 10.93 (br s, 1H), 10.40 (br s, 1H), 8.87 (s, 1H), 8.83 (s, 1H), 8.28 (d, J=1.9 Hz, 1H), 7.09 (d, J=8.7 Hz, 1H), 7.07 (dd, J=8.9, 2.3 Hz, 1H), 5.03 (br s, 1H), 4.74 (br s, 1H), 4.11 (dd, J=9.7, 4.1 Hz, 1H), 4.01 (dd, J=10.0, 5.9 Hz, 1H), 3.92 (br s, 1H), 3.53 (br s, 2H).

EXAMPLE 11

N-[5-chloro-2-(2-methoxy-1-methylethoxy)phenyl]-N'-(5-cyano-2-pyrazinyl)urea

The desired product (11.6 mg, 32%) was prepared by substituting 1-methoxy-2-propanol (9.0 mg, 0.10 mmol) for 2-cyclohexen-1-ol in Example 1G. MS (ESI(−)) m/z 362 (M−H)⁻; ¹H NMR (500 MHz, DMSO-d₆) δ 10.97 (s, 1H), 10.06 (br s, 1H), 8.92 (s, 1H), 8.86 (s, 1H), 8.27 (d, J=2.5 Hz, 1H), 7.17 (d, J=9.0 Hz, 1H), 7.05 (dd, J=8.7, 2.8 Hz, 1H), 4.68–4.74 (m, 1H), 3.62 (dd, J=10.6, 6.2 Hz, 1H), 3.52 (dd, J=10.6, 3.7 Hz, 1H), 3.28 (s, 3H), 1.29 (d, J=6.2 Hz, 3H).

EXAMPLE 12

N-[5-chloro-2-(2-ethoxy-1-methylethoxy)phenyl]-N'-(5-cyano-2-pyrazinyl)urea

The desired product (11.7 mg, 31%) was prepared by substituting 1-ethoxy-2-propanol (10.4 mg, 0.10 mmol) for 2-cyclohexen-1-ol in Example 1G. MS (ESI(−)) m/z 376 (M−H)⁻; ¹H NMR (500 MHz, DMSO-d₆) δ 10.97 (br s, 1H), 10.09 (br s, 1H), 8.92 (s, 1H), 8.86 (s, 1H), 8.27 (d, J=2.5 Hz, 1H), 7.18 (d, J=9.0 Hz, 1H), 7.05 (dd, J=8.7, 2.8 Hz, 1H), 4.65–4.72 (m, 1H), 3.64 (dd, J=10.6, 6.2 Hz, 1H), 3.55 (dd, J=10.8, 4.2 Hz, 1H), 3.42–3.50 (m, 2H), 1.30 (d, J=6.2 Hz, 3H), 1.06 (t, J=7.0 Hz, 3H).

EXAMPLE 13

N-[5-chloro-2-(2-methoxyethoxy)phenyl]-'-(5-cyano-2-pyrazinyl)urea

The desired product (11.5 mg, 33%) was prepared by substituting 2-methoxyethanol (7.6 mg, 0.10 mmol) for 2-cyclohexen-1-ol. MS (ESI(−)) m/z 348 (M−H); ¹H NMR (500 MHz, DMSO-d₆) δ 10.96 (br s, 1H), 10.23 (br s, 1H), 8.92 (s, 1H), 8.83 (s, 1H), 8.26 (d, J=2.5 Hz, 1H), 7.11 (d, J=8.7 Hz, 1H), 7.07 (dd, J=8.7, 2.5 Hz, 1H), 4.22–4.26 (m, 2H), 3.75–3.80 (m, 2H), 3.34 (s, 3H).

EXAMPLE 14

N-[5-chloro-2-(2-isopropoxyethoxy)phenyl]-N'-(5-cyano-2-pyrazinyl)urea

The desired product (9.8 mg, 26%) was prepared by substituting 2-isopropoxyethanol (10.4 mg, 0.10 mmol) for 2-cyclohexen-1-ol in Example 1G. MS (ESI(−)) m/z 376 (M−H)⁻; ¹H NMR (500 MHz, DMSO-d₆) δ 10.94 (s, 1H), 10.3 (br s, 1H), 8.91 (s, 1H), 8.87 (s, 1H), 8.25 (d, J=2.5 Hz, 1H), 7.12 (d, J=8.7 Hz, 1H), 7.07 (dd, J=8.7, 2.5 Hz, 1H), 4.22 (t, J=4.8 Hz, 2H), 3.79 (t, J=4.8 Hz, 2H), 3.63–3.69 (m, 1H), 1.09 (d, J=6.2 Hz, 6H).

EXAMPLE 15

N-[5-chloro-2-(2-ethoxyethoxy)phenyl]-N'-(5-cyano-2-pyrazinyl)urea

The desired product (13.4 mg, 37%) was prepared by substituting 2-ethoxyethanol (9.0 mg, 0.10 mmol) for 2-cyclohexen-1-ol in Example 1G. MS (ESI(−)) m/z 361 (M−H)$^-$; $^1$H NMR (500 MHz, DMSO-d$_6$) δ 10.46 (br s, 1H), 10.31 (br s, 1H), 8.89 (s, 1H), 8.83 (s, 1H), 8.26 (d, J=2.5 Hz, 1H), 7.11 (d, J=9.0 Hz, 1H), 7.07 (dd, J=8.9, 2.7 Hz, 1H), 4.24 (t, J=4.7 Hz, 2H), 3.81 (t, J=4.7 Hz, 2H), 3.53 (dd, J=14.0, 7.2 Hz, 2H), 1.11 (t, J=6.9 Hz, 3H).

EXAMPLE 16

N-{5-chloro-2-[2-(methylsulfanyl)ethoxy]phenyl}-N'-(5-cyano-2-pyrazinyl)urea

The desired product (5.8 mg, 16%) was prepared by substituting 2-(methylsulfanyl)ethanol (9.2 mg, 0.10 mmol) for 2-cyclohexen-1-ol in Example 1G. MS (ESI(−)) m/z 364 (M−H)$^-$; $^1$H NMR (500 MHz, DMSO-d$_6$) δ 10.42 (br s, 1H), 10.14 (br s, 1H), 8.90 (s, 1H), 8.87 (s, 1H), 8.27 (d, J=2.8 Hz, 1H), 7.14 (d, J=8.7 Hz, 1H), 7.07 (dd, J=8.7, 2.5 Hz, 1H), 4.27 (t, J=6.9 Hz, 2H), 2.96 (t, J=6.7 Hz, 2H), 2.15 (s, 3H).

EXAMPLE 17

N-[5-chloro-2-(3-methoxy-3-methylbutoxy)phenyl]-N'-(5-cyano-2-pyrazinyl)urea

The desired product (17.9 mg, 46%) was prepared by substituting 3-methoxy-3-methyl-1-butanol (11.8 mg, 0.10 mmol) for 2-cyclohexen-1-ol in Example 1G. MS (ESI(−)) m/z 390 (M−H)$^-$; $^1$H NMR (500 MHz, DMSO-d$_6$) δ 10.94 (s, 1H), 9.85 (br s, 1H), 9.00 (s, 1H), 8.83 (s, 1H), 8.24 (d, J=2.5 Hz, 1H), 7.11 (d, J=8.7 Hz, 1H), 7.06 (dd, J=8.7, 2.8 Hz, 1H), 4.15 (t, J=7.3 Hz, 2H), 3.13 (s, 3H), 2.05 (t, J=7.3 Hz, 2H), 1.19 (s, 6H).

EXAMPLE 18

N-{5-chloro-2-[2-(2-methoxyethoxy)ethoxy]phenyl}-N'-(5-cyano-2-pyrazinyl)urea

The desired product (12.2 mg, 31%) was prepared by substituting 2-(2-methoxyethoxy)ethanol (12.0 mg, 0.10 mmol) for 2-cyclohexen-1-ol in Example 1G. MS (ESI(−)) m/z 392 (M−H)$^-$; $^1$H NMR (500 MHz, DMSO-d$_6$) δ 10.94 (br s, 1H), 10.41 (br s, 1H), 8.83–8.89 (m, 2H), 8.26 (d, J=2.5 Hz, 1H), 7.12 (d, J=8.7 Hz, 1H), 7.07 (dd, J=8.7, 2.5 Hz, 1H), 4.21–4.27 (m, 2H), 3.83–3.88 (m, 2H), 3.59–3.64 (m, 2H), 3.41–3.47 (m, 2H), 3.21 (s, 3H).

EXAMPLE 19

N-[2-(allyloxy)-5-chlorophenyl]-N'-(5-cyano-2-pyrazinyl)urea

The desired product (7.2 mg, 22%) was prepared by substituting 2-propen-1-ol (6.0 mg, 0.10 mmol) for 2-cyclohexen-1-ol in Example 1G. MS (ESI(−)) m/z 328 (M−H)$^-$; $^1$H NMR (500 MHz, DMSO-d$_6$) δ 10.88 (br s, 1H), 10.04 (br s, 1H), 8.98 (d, J=1.5 Hz, 1H), 8.83 (d, J=1.5 Hz, 1H), 8.26 (d, J=2.5 Hz, 1H), 7.08 (d, J=8.6 Hz, 1H), 7.07 (dd, J=8.6, 2.5 Hz, 1H), 6.08–6.18 (m, 1H), 5.44–5.49 (m, 1H), 5.34–5.38 (m, 1H), 4.72 (dt, J=5.5, 1.5 Hz, 2H).

EXAMPLE 20

N-(5-chloro-2-{2-[3-(6-methyl-2-pyridinyl)propoxy]ethoxy}phenyl)-N'-(5-cyano-2-pyrazinyl)urea The desired product (6.4 mg, 11%) was prepared by substituting 2-[3-(6-methyl-2-pyridinyl)propoxy]ethanol (19.5 mg, 0.10 mmol) for 2-cyclohexen-1-ol in Example 1G. MS (ESI(−)) m/z 465 (M−H)$^-$; $^1$H NMR (500 MHz, DMSO-d$_6$) δ 10.93 (s, 1H), 10.26 (br s, 1H), 8.88 (s, 1H), 8.82 (s, 1H), 8.25 (d, J=2.5 Hz, 1H), 8.12 (br s, 1H), 7.53 (br s, 2H), 7.11 (d, J=8.7 Hz, 1H), 7.08 (dd, J=8.7, 2.5 Hz, 1H), 4.23 (t, J=4.7 Hz, 2H), 3.82 (t, J=4.5 Hz, 2H), 3.54 (t, J=6.2 Hz, 2H), 2.90 (t, J=7.6 Hz, 2H), 2.58 (s, 3H), 1.90–1.98 (m, 2H).

EXAMPLE 21

N-{5-chloro-2-[(3-methyl-2-butenyl)oxy]phenyl}-N'-(5-cyano-2-pyrazinyl)urea

The desired product (7.9 mg, 22%) was prepared by substituting 3-methyl-2-buten-1-ol (8.6 mg, 0.10 mmol) for 2-cyclohexen-1-ol in Example 1G. MS (ESI(−)) m/z 356 (M−H)$^-$; $^1$H NMR (500 MHz, DMSO-d$_6$) δ 10.92 (br s, 1H), 10.13 (br s, 1H), 8.96 (s, 1H), 8.76 (s, 1H), 8.24 (d, J=2.5 Hz, 1H), 7.10 (d, J=8.7 Hz, 1H), 7.06 (dd, J=8.6, 2.7 Hz, 1H), 5.54 (t, J=6.7 Hz, 1H), 4.67 (s, 1H), 4.66 (s, 1H), 1.80 (s, 3H), 1.73 (s, 3H).

EXAMPLE 22

N-[5-chloro-2-(3-pentynyloxy)phenyl]-N'-(5-cyano-2-pyrazinyl)urea

The desired product (3.9 mg, 11%) was prepared by substituting 3-pentyn-1-ol (8.4 mg, 0.10 mmol) for 2-cyclohexen-1-ol in Example 1G. MS (ESI(−)) m/z 354 (M−H)$^-$; $^1$H NMR (500 MHz, DMSO-d$_6$) δ 10.95 (br s, 1H), 10.33 (br s, 1H), 8.89 (s, 1H), 8.87 (s, 1H), 8.28 (d, J=2.5 Hz, 1H), 7.11 (d, J=8.7 Hz, 1H), 7.07 (dd, J=8.7, 2.5 Hz, 1H), 4.16 (t, J=6.7 Hz, 2H), 2.68–2.76 (m, 2H), 1.71 (t, J=2.5 Hz, 3H).

EXAMPLE 23

N-[5-chloro-2-(2-oxo-2-phenylethoxy)phenyl]-N'-(5-cyano-2-pyrazinyl)urea

The desired product (3.7 mg, 9%) was prepared by substituting 2-hydroxy-1-phenylethanone (13.6 mg, 0.10 mmol) for 2-cyclohexen-1-ol in Example 1G. MS (ESI(−)) m/z 406 (M−H)$^-$; $^1$H NMR (500 MHz, DMSO-d$_6$) δ 10.90 (s, 1H), 10.58 (s, 1H), 8.92 (s, 1H), 8.90 (s, 1H), 8.30 (d, J=2.5 Hz, 1H), 8.05 (s, 1H), 8.04 (s, 1H), 7.71 (t, J=7.3 Hz, 1H), 7.59 (t, J=7.8 Hz, 2H), 7.08 (d, J=8.7 Hz, 1H), 7.03 (dd, J=8.7, 2.5 Hz, 1H), 5.82 (s, 2H).

EXAMPLE 24

N-[5-chloro-2-(3-cyclopenten-1-yloxy)phenyl]-N'-(5-cyano-2-pyrazinyl)urea

The desired product (23 mg, 20.4%) was prepared by substituting 3-cyclopenten-1-ol (24 mg, 0.30 mmol) for 2-cyclohexen-1-ol in Example 1G. MS (ESI(−)) m/z 354

(M–H)⁻; ¹H NMR (500 MHz, DMSO-d₆) δ 10.90 (s, 1H), 9.84 (s, 1H), 8.92 (s, 1H), 8.96 (s, 1H), 8.75 (s, 1H), 8.27 (s, 1H), 7.06–7.08 (m, 2H), 5.82 (br s, 2H), 5.14–5.18 (m, 1H), 2.89 (d, J=6.86 Hz, 1H), 2.86 (d, J=6.86 Hz, 1H), 2.55 (br s, 1H), 2.50 (br s, 1H).

EXAMPLE 25

N-(5-chloro-2-{[(3R,4S)-3,4-dihydroxycyclopentyl]oxy}phenyl)-N'-(5-cyano-2-pyrazinyl)urea

EXAMPLE 25A 4-chloro-1-(3-cyclopenten-1-yloxy)-2-nitrobenzene

A mixture of 2-nitro-4-chlorophenol (3.46 g, 20 mmol), 3-cyclopenten-1-ol (2.1 g, 24 mmol), triphenylphosphine on polystyrene (3.0 mmol per gram, 10 g, 30 mmol) and di-tert-butyl azadicarboxylate (6.9 g, 30 mmol) in THF (200 mL) was shaken for 1 hour and filtered. The resin was washed with dichloromethane (4×50 mL). The combined organic solutions were mixed with 20 g of silica gel and then concentrated to dryness. The residue was purified by flash column chromatography on silica gel with 15% ethyl acetate/hexanes to provide 4.08 g (85%) of the desired product. ¹H NMR (300 MHz, CDCl₃) δ 7.80 (d, J=2.4 Hz, 1H), 7.46 (dd, J=8.8, 2.7 Hz, 1H), 7.00 (d, J=8.8 Hz, 1H), 5.75 (br s, 2H), 5.03–5.13 (m, 1H), 2.87 (d, J=6.8 Hz, 1H), 2.82 (d, J=6.8 Hz, 1H), 2.65 (br s, 1H), 2.59 (br s, 1H).

EXAMPLE 25B (1R,2S)-4-(4-chloro-2-nitrophenoxy)-1,2-cyclopentanediol

A solution of Example 25A (1.2 g, 5.0 mmol) and N-methylmorpholine oxide (0.7 g, 6.0 mmol) in THF (18 mL) and water (2.0 mL) was treated with osmium tetroxide (2.5% wt in tert-butanol, 1.0 mL), stirred at room temperature for 1 hour, and concentrated. The residue was purified by flash column chromatography on silica gel with ethyl acetate to provide 0.7 g (51%) of the desired product. MS (DCI/NH₃) m/z 291 (M+NH₄)⁺; ¹H NMR spectrum indicated a mixture of two isomers in a 3:1 ratio. The ¹H NMR spectrum of the major isomer (300 MHz, CDCl₃) δ 7.80 (d, J=2.7 Hz, 1H), 7.47 (dd, J=8.8, 2.7 Hz, 1H), 7.47 (d, J=8.8 Hz, 1H), 4.95–5.05 (m, 1H), 4.30–4.40 (m, 2H), 2.05–2.30 (m, 4H).

EXAMPLE 25C phenyl 5-cyano-2-pyrazinylcarbamate

A solution of Example 1B (6.0 g, 50 mmol) in a mixture of dichloromethane (100 mL) and THF (200 mL) in a room temperature water bath was treated with pyridine (4.45 mL, 55 mmol), treated dropwise with phenyl chloroformate (10.0 mL, 80 mmol), and stirred at room temperature overnight. The mixture was treated with ethyl acetate (500 mL) and filtered. The filter cake was washed with ethyl acetate and the combined filtrates were washed with brine, dried (MgSO₄), filtered, and concentrated. The concentrate was triturated with 30% ethyl acetate/hexanes to provide 8.50 g (70.8%) of the desired product. MS (APCI(+)) m/z 241 (M+H)⁺; ¹H NMR (300 MHz, DMSO-d₆) δ 11.76 (s, 1H), 9.20 (s, 1H), 8.98 (s, 1H), 7.20–7.50 (m, 5H).

EXAMPLE 25D

N-(5-chloro-2-{[(3R,4S)-3,4-dihydroxycyclopentyl]oxy}phenyl)-N'-(5-cyano-2-pyrazinyl)urea A solution of Example 25B (100 mg, 0.37 mmol) in absolute ethanol (5.0 mL) was treated with Raney Ni (water suspension, 100 mg) and hydrazine monohydrate (0.1 mL), stirred for 1 hour, and filtered through diatomaceous earth (Celite®). The Celite® pad was washed with ethyl acetate and the combined filtrates were mixed with silica gel (2 g) and concentrated to dryness. The concentrate was purified by flash column chromatography on silica gel with 1% methanol/ethyl acetate. The resulting oil (60 mg) was dissolved in toluene (5.0 mL), treated with Example 25C (60 mg, 0.25 mmol), heated to reflux overnight, and cooled to room temperature. The mixture was filtered and the filter cake was washed with 30% ethyl acetate/hexanes (3×10 mL) and ethyl acetate (3×5 mL), and dried under vacuum to provide 65 mg (45% yield for two steps) of the desired product. MS (ESI(–)) m/z 388 (M–H)⁻; ¹H NMR (500 MHz, DMSO-d₆) δ 10.98 (s, 1H), 9.86 (s, 1H), 8.94 (s, 1H), 8.79 (s, 1H), 8.26 (d, J=2.5 Hz, 1H), 7.4 (dd, J=8.6, 2.5 Hz, 1H), 6.98 (d, J=8.6 Hz, 1H), 4.90–5.00 (m, 1H), 4.55 (d, J=4.3 Hz, 2H), 4.05–4.13 (m, 2H), 2.10–2.20 (m, 2H), 1.90–1.98 (m, 2H).

EXAMPLE 26

N-(5-chloro-2-{[(1S,3R)-3-hydroxycyclopentyl]oxy}phenyl)-N'-(5-cyano-2-pyrazinyl)urea

EXAMPLE 26A 3-(4-chloro-2-nitrophenoxy)cyclopentanol

A solution of Example 25A (1.18 g, 5 mmol) in THF (20 mL) was treated with a solution of 9-BBN (0.5M in THF, 10 mL, 5.0 mmol) via syringe. After stirring at room temperature overnight, the solution was cooled with an ice bath, treated with a solution of NaOH (0.2 g) in water (2 mL), treated dropwise with hydrogen peroxide (30% wt, 0.56 g, 5.0 mmol), and stirred for 3 hours. The mixture was treated with water (50 mL) and ethyl acetate (150 mL) and the organic phase was extracted with ethyl acetate. The combined organic extracts were dried (MgSO₄), filtered, and concentrated. The concentrate was purified by flash column chromatography on silica gel with 60% ethyl acetate/hexanes to provide 0.55 g (42.8%) of the desired product. MS (DCI/NH₃) m/z 275 (M+NH₄)⁺; ¹H NMR indicated two isomers in ~4:1 ratio. The spectrum of the major isomer (300 MHz, CDCl₃) δ 7.79 (d, J=2.4 Hz, 1H), 7.46 (dd, J=8.8, 2.7 Hz, 1H), 7.01 (d, J=8.8 Hz, 1H), 4.95–5.05 (m, 1H), 4.55–4.60 (m, 1H), 1.4–2.30 (m, 7H).

EXAMPLE 26B

N-(5-chloro-2-{[(1S,3R)-3-hydroxycyclopentyl]oxy}phenyl)-N'-(5-cyano-2-pyrazinyl)urea The desired product (275 mg, 49.3% yield for two steps) was prepared by substituting Example 26A for Example 25A in Example 25D. MS (ESI(–)) m/z 372 (M–H)⁻; ¹H NMR (500 MHz, DMSO-d₆) δ 10.98 (s, 1H), 9.83 (s, 1H), 8.93 (s, 1H), 8.78 (s, 1H), 8.26 (d, J=2.5 Hz, 1H), 7.05 (dd, J=8.7, 2.5 Hz, 1H), 7.01(d, J=8.7 Hz, 1H), 4.95–5.00 (m, 1H), 4.65

(d, J=3.7 Hz, 1H), 4.32–4.36 (m, 1H), 2.48–2.53 (m, 1H), 2.18–2.26 (m, 1H), 1.90–2.02 (m, 2H), 1.73–1.78 (m, 1H), 1.54–1.60 (m, 1H).

EXAMPLE 27

N-{2-[bis(2-methoxyethyl)amino]-5-bromophenyl}-N'-(5-cyano-2-pyrazinyl)urea

EXAMPLE 27A

N-(2-amino-4-bromophenyl)-N,N-bis(2-methoxyethyl)amine

A mixture of 4-bromo-1-fluoro-2-nitrobenzene (0.44 g, 2mmol) and N,N-bis(2-methoxyethyl)amine (0.266 g, 2.4 mmol) in acetonitrile (10 mL) in a capped 20 mL vial was shaken at 80° C. overnight and concentrated. The concentrate was dissolved in methanol (10 mL), and treated with Raney nickel (50% water suspension, 0.40 g, 6.8 mmol). The vial was filled with excessive hydrogen, shaken at 50° C. for 1 hour, filtered, and concentrated. The concentrate was purified by preparative HPLC with acetonitrile/water containing 0.1% TFA to provide the desired product. MS (APCI(+)) m/z 304 (M+H)$^+$.

EXAMPLE 27B

N-{2-[bis(2-methoxyethyl)amino]-5-bromophenyl}-N'-(5-cyano-2-pyrazinyl)urea

A mixture of Example 25C (24 mg, 0.10 mmol) and Example 27A (25.8 mg, 0.10 mmol) in toluene (2.5 mL) in a 4-mL capped vial was shaken at 110° C. for 3 hours and concentrated. The concentrate was purified by preparative HPLC to provide 11.2 mg (20%) of the desired product. MS (ESI(−)) m/z 447 (M−H)$^-$; $^1$H NMR (500 MHz, DMSO-d$_6$) δ 11.00 (s, 1H), 10.52 (br s, 1H), 8.90 (s, 1H), 8.89 (s, 1H), 8.41 (d, J=2.5 Hz, 7.31 (d, J=8.7 Hz, 1H), 7.22 (dd, J=8.4, 2.2 Hz, 1H), 3.30 (t, J=6.6 Hz, 4H), 3.17 (t, J=6.1 Hz, 4H), 3.11 (s, 6H).

EXAMPLE 28

N-{5-bromo-2-[ethyl(2-methoxyethyl)amino]phenyl}-N'-(5-cyano-2-pyrazinyl)urea

The desired product (11.2 mg, 21%) was prepared by substituting N-ethyl-N-(2-methoxyethyl)amine (20.6 mg, 0.2 mmol) for N,N-bis(2-methoxyethyl)amine in Example 27. MS (ESI(−)) m/z 419 (M−H)$^-$; $^1$H NMR (500 MHz, DMSO-d$_6$) δ 11.01 (s, 1H), 10.57 (br s, 1H), 8.91 (s, 1H), 8.90 (s, 1H), 8.43 (d, J=2.5 Hz, 1H), 7.28 (d, J=8.4 Hz, 1H), 7.22 (dd, J=8.6, 2.3 Hz, 1H), 3.29 (t, J=5.0 Hz, 2H), 3.10 (t, J=5.9 Hz, 2H), 3.10 (s, 3H), 3.03 (dd, J=14.2, 7.0 Hz, 2H), 0.89 (t, J=7.0 Hz, 3H).

EXAMPLE 29

N-{2-[benzyl(2-hydroxyethyl)amino]-5-bromophenyl}-N'-(5-cyano-2-pyrazinyl)urea

The desired product (3.5 mg, 6%) was prepared by substituting 2-(benzylamino)ethanol (30.2 mg, 0.2 mmol) for N,N-bis(2-methoxyethyl)amine in Example 27. MS (ESI (−)) m/z 467 (M−H)$^-$; $^1$H NMR (500 MHz, DMSO-d$_6$) δ 10.95 (s, 1H), 10.48 (br s, 1H), 8.90 (s, 1H), 8.81 (s, 1H), 8.32 (s, 1H), 7.12–7.25 (m, 7H), 4.24 (s, 2H), 3.50 (t, J=6.4 Hz, 2H), 3.05 (t, J=6.2 Hz, 2H).

EXAMPLE 30

N-{5-bromo-2-[(2-hydroxy-2-phenylethyl)(methyl)amino]phenyl}-N'-(5-cyano-2-pyrazinyl)urea The desired product (11.6 mg, 20%) was prepared by substituting 2-(methylamino)-1-phenylethanol (30.2 mg, 0.2 mmol) for N,N-bis(2-methoxyethyl)amine in Example 27. MS (ESI(−)) m/z 465 (M−H)$^-$; $^1$H NMR (500 MHz, DMSO-d$_6$) δ 10.74 (s, 1H), 10.46 (br s, 1H), 8.84 (s, 1H), 8.74 (s, 1H), 8.41 (d, J=2.2 Hz, 1H), 7.29 (d, J=8.4 Hz, 1H), 7.14–7.24 (m, 5H), 7.06 (t, J=7.2 Hz, 1H), 4.55–4.62 (m, 1H), 3.08–3.19 (m, 3H), 2.67 (s, 3H).

EXAMPLE 31

N-{2-[bis(2-methoxyethyl)amino]-5-chlorophenyl}-N'-(5-cyano-2-pyrazinyl)urea

EXAMPLE 31A

N-(2-amino-4-chlorophenyl)-N,N-bis(2-methoxyethyl)amine

A mixture of 4-chloro-1-fluoro-2-nitrobenzene (35.1 mg, 0.2 mmol) and N,N-bis(2-methoxyethyl)amine (0.266 g, 2.4 mmol) in acetonitrile (10 mL) in a capped 20-mL-vial was shaken at 80° C. overnight and concentrated. The concentrate was dissolved in methanol (10 mL), treated with Raney nickel (50% water suspension, 0.40 g, 6.8 mmol), filled with excess hydrogen, shaken at 50° C. for 1 hour, and filtered. The filtrate was concentrate and the concentrate was purified by HPLC with acetonitrile/water containing 0.1% TFA to provide the desired product. MS (APCI(+)) m/z 260 (M+H)$^+$.

EXAMPLE 31B

N-{2-[bis(2-methoxyethyl)amino]-5-chlorophenyl}-N'-(5-cyano-2-pyrazinyl)urea

A mixture of Example 25C (24 mg, 0.10 mmol) and Example 31A (25.8 mg, 0.10 mmol) in toluene (2.5 mL) in a 4-mL capped vial was shaken at 110° C. for 3 hours and concentrated. The concentrate was purified by preparative HPLC with acetonitrile/water containing 0.1% TFA to provide 5.7 mg (11%) of the desired product. MS (ESI(−)) m/z 403 (M−H)$^-$; $^1$H NMR (500 MHz, DMSO-d$_6$) δ 11.00 (s, 1H), 10.53 (br s, 1H), 8.90 (s, 1H), 8.89 (s, 1H), 8.28 (d, J=2.8 Hz, 1H), 7.37 (d, J=8.4 Hz, 1H), 7.09 (dd, J=8.7, 2.5 Hz, 1H), 3.30 (t, J=6.1 Hz, 4H), 3.17 (t, J=5.9 Hz, 4H), 3.11 (s, 6H).

EXAMPLE 32

N-{5-chloro-2-[ethyl(2-methoxyethyl)amino]phenyl}-N'-(5-cyano-2-pyrazinyl)urea

The desired product (5.4 mg, 11%) was prepared by substituting N-ethyl-N-(2-methoxyethyl)amine (20.6 mg, 0.2 mmol) for N,N-bis(2-methoxyethyl)amine in Example 31. MS (ESI(−)) m/z 373 (M−H)$^-$. $^1$H NMR (500 MHz, DMSO-d$_6$) δ 11.01 (s, 1H), 10.59 (br s, 1H), 8.91 (s, 1H), 8.90 (s, 1H), 8.29 (d, J=2.5 Hz, 1H), 7.34 (d, J=8.4 Hz, 1H), 7.10 (dd, J=8.4, 2.5 Hz, 1H), 3.29 (t, J=5.9 Hz, 2H), 3.10 (t, J=6.1 Hz, 2H), 3.10 (s, 3H), 3.03 (dd, J=14.2, 7.0 Hz, 2H), 0.89 (t, J=7.0 Hz, 3H).

EXAMPLE 33

N-{2-[benzyl(2-hydroxyethyl)amino]-5-chlorophenyl}-N'-(5-cyano-2-pyrazinyl)urea

The desired product (1.6 mg, 3%) was prepared by substituting 2-(benzylamino)ethanol (30.2 mg, 0.2 mmol) for N,N-bis(2-methoxyethyl)amine in Example 31. MS (ESI (−)) m/z 421 (M−H)$^-$; $^1$H NMR (500 MHz, DMSO-d$_6$) δ 10.96 (s, 1H), 10.50 (br s, 1H), 8.90 (s, 1H), 8.81 (s, 1H), 8.18 (d, J=2.5 Hz, 1H), 7.13–7.27 (m, 6H), 7.00 (dd, J=8.4, 2.5 Hz, 1H), 4.54 (t, J=5.3 Hz, 1H), 4.23 (s, 2H), 3.50 (dd, J=11.5, 6.2 Hz, 2H), 3.05 (t, J=6.4 Hz, 2H).

EXAMPLE 34

N-{5-chloro-2-[(2-hydroxy-2-phenylethyl)(methyl) amino]phenyl}-N'-(5-cyano-2-pyrazinyl)urea The desired product (4.8 mg, 9%) was prepared by substituting 2-(methylamino)-1-phenylethanol (30.2 mg, 0.2 mmol) for N,N-bis(2-methoxyethyl)amine in Example 31. MS (ESI(−)) m/z 421 (M−H)$^-$; $^1$H NMR (500 MHz, DMSO-d$_6$) δ 10.75 (s, 1H), 10.48 (br s, 1H), 8.84 (s, 1H), 8.74 (s, 1H), 8.28 (d, J=2.5 Hz, 1H), 7.35 (d, J=8.4 Hz, 1H), 7.14–7.34 (m, 4H), 7.04–7.11 (m, 2H), 4.55–4.61 (m, 1H), 3.08–3.20 (m, 2H), 2.67 (s, 3H).

EXAMPLE 35

N-{2-[bis(2-methoxyethyl)amino]-5-cyanophenyl}-N'-(5-cyano-2-pyrazinyl)urea

EXAMPLE 35A 3-amino-4-[bis(2-methoxyethyl)amino]benzonitrile

A mixture of 4-cyano-1-fluoro-2-nitrobenzene (35.1 mg, 0.2 mmol) and N,N-bis(2-methoxyethyl)amine (0.266 g, 2.4 mmol) in acetonitrile (10 mL) in a capped 20-mL vial was shaken at 80° C. overnight and concentrated. The concentrate was dissolved in methanol (10 mL), treated with Raney nickel (50% water suspension, 0.40 g, 6.8 mmol), filled with excess hydrogen, shaken at 50° C. for 1 hour, and filtered. The filtrate was concentrated and the concentrate was purified by HPLC with acetonitrile/water containing 0.1% TFA to give the desired compound. MS (APCI(+)) m/z 250 (M+H)$^+$.

EXAMPLE 35B

N-{2-[bis(2-methoxyethyl)amino]-5-cyanophenyl}-N'-(5-cyano-2-pyrazinyl)urea

A mixture of Example 25C (24 mg, 0.10 mmol) and Example 35A (23 mg, 0.10 mmol) in toluene (2.5 mL) in a 4-mL capped vial was shaken at 110° C. for 3 hours and concentrated. The concentrate was purified by preparative HPLC with acetonitrile/water containing 0.1% TFA to provide 3.0 mg (6%) of the desired product. MS (ESI(−)) m/z 394 (M−H)$^-$; H NMR (500 MHz, DMSO-d$_6$) δ 11.00 (s, 1H), 10.46 (br s, 1H), 8.89 (s, 2H), 8.48–8.52 (m, 1H), 7.45–7.53 (m, 2H), 3.34 (t, J=5.8 Hz, 4H), 3.28 (t, J=5.6 Hz, 4H), 3.12 (s, 6H).

EXAMPLE 36

N-{5-cyano-2-[(2-hydroxy-2-phenylethyl)(methyl) amino]phenyl}-N-(5-cyano-2-pyrazinyl)urea The desired product (2.1 mg, 4%) was prepared by substituting 2-(methylamino)-1-phenylethanol (30.2 mg, 0.2 mmol) for N,N-bis(2-methoxyethyl) in Example 35. MS (ESI(−)) m/z 412 (M−H)$^-$; $^1$H NMR (500 MHz, DMSO-d$_6$) δ 10.73 (s, 1H), 10.31 (s, 1H), 8.89 (s, 1H), 8.78 (s, 1H), 8.44 (d, J=1.9 Hz, 1H), 7.49 (dd, J=8.3, 2.0 Hz, 1H), 7.40 (d, J=8.4 Hz, 1H), 7.17–7.26 (m, 4H), 7.09–7.13 (m, 1H), 5.38–5.46 (m, 1H), 4.66–4.73 (m, 1H), 3.16–3.26 (m, 2H), 2.80 (s, 3H).

EXAMPLE 37

N-[5-chloro-2-(2-chloro-1-methoxyethoxy)phenyl]-N'-(5-cyano-2-pyrazinyl)urea

The desired product (2.8 mg, 7%) was prepared by substituting 2-chloro-1-methoxyethanol (12.5 mg, 0.10 mmol) for 2-cyclohexen-1-ol in Example 1. MS (ESI(−)) m/z 394 (M−H)$^-$; $^1$H NMR (500 MHz, DMSO-d$_6$) δ 10.99 (s, 1H), 10.14 (br s, 1H), 8.90 (s, 1H), 8.88 (s, 1H), 8.29 (d, J=2.5 Hz, 1H), 7.25 (d, J=9.0 Hz, 1H), 7.08 (dd, J=8.7, 2.8 Hz, 1H), 4.79–4.86 (m, 1H), 3.97 (dd, J=11.9, 4.1 Hz, 1H), 3.90 (dd, J=12.0, 6.1 Hz, 1H), 3.28 (s, 3H).

EXAMPLE 38

N-[2-(3-aminopropoxy)-5-chlorophenyl]-N'-(5-cyano-2-pyrazinyl)urea

EXAMPLE 38A tert-butyl 3-[4-chloro-2-({[(5-cyano-2-pyrazinyl) amino]carbonyl}amino)phenoxy]propylcarbamate The desired product was prepared by substituting tert-butyl 3-hydroxypropylcarbamate (17.5 mg, 0.10 mmol) for 2-cyclohexen-1-ol in Example 1.

EXAMPLE 38B

N-[2-(3-aminopropoxy)-5-chlorophenyl]-N'-(5-cyano-2-pyrazinyl)urea

A solution of Example 38A in trifluoroacetic acid (0.1 mL) and dichloromethane (0.9 mL) was stirred at room temperature for 3 hours and concentrated. The concentrate was purified by HPLC with acetonitrile/water containing 0.1% TFA to provide 2.8 mg (6%) of the desired product. MS (ESI(−)) m/z 347 (M−H)$^-$; $^1$H NMR (500 MHz, DMSO-d$_6$) δ 10.93 (br s, 1H), 10.09 (br s, 1H), 8.91 (s, 1H), 8.85 (s, 1H), 8.26 (d, J=2.5 Hz, 1H), 7.71 (br s, 2H), 7.12 (dd, J=8.7, 2.2 Hz, 1H), 7.10 (d, J=8.7 Hz, 1H), 4.20 (t, J=6.2 Hz, 2H), 3.03 (br s, 2H), 2.10 (m, 2H).

EXAMPLE 39

N-{5-chloro-2-[3-(dimethylamino)propoxy]phenyl}-N'-(5-cyano-2-pyrazinyl)urea

The desired product (2.4 mg, 5%) was prepared by substituting 3-(dimethylamino)-1-propanol (10.3 mg, 0.10 mmol) for 2-cyclohexen-1-ol in Example 1. MS (ESI(−))

m/z 373 (M−H)⁻; ¹H NMR (500 MHz, DMSO-d₆) δ 10.90 (br s, 1H), 10.03 (br s, 1H), 8.94 (s, 1H), 8.87 (s, 1H), 8.24 (d, J=1.9 Hz, 1H), 7.05–7.16 (m, 2H), 4.18 (t, J=6.2 Hz, 2H), 3.29–3.34 (m, 2H), 2.72 (br s, 6H), 2.11–2.23 (m, 2H).

EXAMPLE 40 ethyl 2-{[4-chloro-2-({[(5-cyano-2-pyrazinyl) amino] carbonyl}amino)phenoxy] methyl}cyclopropanecarboxylate The desired product (2.5 mg, 6%) was prepared by substituting ethyl 2-(hydroxymethyl)cyclopropanecarboxylate (14.4 mg, 0.10 mmol) for 2-cyclohexen-1-ol in Example 1. MS (ESI(−)) m/z 414 (M−H)⁻; ¹H NMR (500 MHz, DMSO-d₆) δ 10.95 (s, 1H), 10.20 (br s, 1H), 8.91 (s, 1H), 8.77 (s, 1H), 8.24–8.28 (m, 1H), 7.04–7.11 (m, 2H), 4.12–4.18 (m, 1H), 3.96–4.08 (m, 3H), 1.82–1.92 (m, 1H), 1.73–1.79 (m, 1H), 1.10–1.19 (m, 4H), 1.02–1.08 (m, 1H).

EXAMPLE 41 ethyl 6-[4-chloro-2-({[(5-cyano-2-pyrazinyl)amino] carbonyl}amino)phenoxy]hexanoate The desired product (4.3 mg, 10%) was prepared by substituting ethyl 6-hydroxyhexanoate (16.0 mg, 0.10 mmol) for 2-cyclohexen-1-ol in Example 1. MS (ESI(−)) m/z 430 (M−H)⁻; ¹H NMR (500 MHz, DMSO-d₆) δ 10.96 (s, 1H), 10.04 (br s, 1H), 8.93 (s, 1H), 8.82 (s, 1H), 8.25 (d, J=2.2 Hz, 1H), 7.09 (d, J=9.0 Hz, 1H), 7.06 (dd, J=8.7, 2.5 Hz, 1H), 4.09 (t, J=6.6 Hz, 2H), 4.01 (dd, J=14.2, 7.0 Hz, 2H), 2.28 (t, J=7.3 Hz, 2H), 1.79–1.87 (m, 2H), 1.56–1.65 (m, 2H), 1.41–1.49 (m, 2H), 1.14 (t, J=7.2 Hz, 3H).

EXAMPLE 42

N-{5-chloro-2-[2-(dimethylamino)-1-methylethoxy] phenyl}-N'-(5-cyano-2-pyrazinyl)urea The desired product (2.9 mg, 6%) was prepared by substituting 1-(dimethylamino)-2-propanol (10.3 mg, 0.10 mmol) for 2-cyclohexen-1-ol in Example 1. MS (ESI(−)) m/z 373 (M−H)⁻; ¹H NMR (500 MHz, DMSO-d₆) δ 10.90 (s, 1H), 9.90 (br s, 1H), 8.96 (s, 1H), 8.95 (s, 1H), 8.29 (d, J=2.5 Hz, 1H), 7.28 (d, J=8.7 Hz, 1H), 7.15 (dd, J=8.7, 2.5 Hz, 1H), 3.96–4.07 (m, 1H), 3.42–3.55 (m, 2H), 2.88 (s, 6H), 1.26 (d, J=5.9 Hz, 3H).

EXAMPLE 43

N-(5-chloro-2-{2-[(2-cyanoethyl)(phenyl)amino] ethoxy}phenyl)-N'-(5-cyano-2-pyrazinyl)urea The desired product (2.9 mg, 5%) was prepared by substituting 3-[(2-hydroxyethyl)phenyl)amino]propanenitrile (19.0 mg, 0.10 mmol) for 2-cyclohexen-1-ol in Example 1. MS (ESI(−)) m/z 460 (M−H)⁻; ¹H NMR (500 MHz, DMSO-d₆) δ 10.90 (br s, 1H), 10.06 (s, 1H), 8.92 (s, 1H), 8.80 (s, 1H), 8.23 (d, J=2.8 Hz, 1H), 7.17 (dd, J=8.9, 7.3 Hz, 2H), 7.11 (d, J=9.0 Hz, 1H), 7.06 (dd, J=8.7, 2.5 Hz, 1H), 6.79 (d, J=7.8 Hz, 1H), 6.66 (t, J=7.2 Hz, 1H), 4.27 (t, J=6.1 Hz, 2H), 3.87 (t, J=6.2 Hz, 2H), 3.72 (t, J=6.9 Hz, 2H), 2.71 (t, J=6.9 Hz, 2H).

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

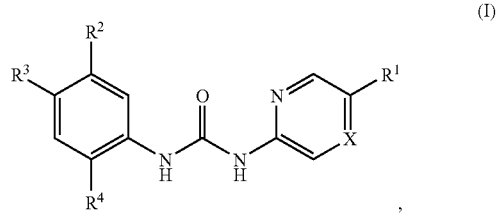

or a therapeutically acceptable salt thereof, wherein
X is —N— or —CH—;
R¹ is selected from the group consisting of hydrogen, alkoxy, alkyl, amino, carboxy, cyano, halo, hydroxy, and hydroxyalkyl;
R² is selected from the group consisting of cyano and halo;
R³ is selected from the group consisting of hydrogen, alkoxy, alkyl, amino, aminoalkyl, aminocarbonyl, arylalkyl, cyano, nitro, —CO₂R⁵, —COR⁵, and —SR⁵;
R⁴ is selected from the group consisting of —(CHR⁶)ₘOR⁷, and —(CH₂)ₙNR⁸R⁹;
R⁵ is selected from the group consisting of hydrogen, alkenyl, alkyl, aryl, arylalkyl, cycloalkyl, and (cycloalkyl)alkyl;
R⁶ is selected from the group consisting of hydrogen, alkyl, aryl, and heteroaryl;
R⁷ is selected from the group consisting of hydrogen, alkenyl, alkoxyalkoxyalkyl, alkoxyalkyl, alkoxycarbonylalkyl, alkylsulfanylalkyl, alkynyl, arylalkyl, arylcarbonylalkyl, aryloxyalkyl, arylsulfanylalkyl, cycloalkenyl, (cycloalkenyl)alkyl, cycloalkyl, (cycloalkyl) alkyl, heteroarylalkoxyalkyl, heteroarylalkyl, (heterocyclyl)alkoxyalkyl, and hydroxyalkyl;
R⁸ and R⁹ are independently selected from the group consisting of hydrogen, alkenyl, alkoxyalkyl, alkyl, alkylsulfanylalkyl, alkynyl, aminoalkyl, arylalkyl, cycloalkenyl, (cycloalkenyl)alkyl, cycloalkyl, (cycloalkyl)alkyl, heteroarylalkyl, (heterocyclyl)alkyl, and hydroxyalkyl;
m is 0–6; provided that when R⁷ is hydrogen m is other than 0; and
n is 0–6; provided that when R⁸ and R⁹ are both hydrogen, n is other than 0.

2. The compound of claim 1 wherein X is —N—.

3. The compound of claim 1 wherein R⁴ is —(CH₂)ₙNR⁸R⁹.

4. The compound of claim 3 wherein n is 0.

5. The compound of claim 4 wherein one of R⁸ and R⁹ is alkoxyalkyl and the other is selected from the group consisting of alkoxyalkyl and alkyl.

6. The compound of claim 5 selected from the group consisting of
N-{2-[bis(2-methoxyethyl)amino]-5-bromophenyl}-N'-(5-cyano-2-pyrazinyl)urea;

N-{5-bromo-2-[ethyl(2-methoxyethyl)amino]phenyl}-N'-(5-cyano-2-pyrazinyl)urea;

N-{2-[bis(2-methoxyethyl)amino]-5-chlorophenyl}-N'-(5-cyano-2-pyrazinyl)urea;

N-{5-chloro-2-[ethyl(2-methoxyethyl)amino]phenyl}-N'-(5-cyano-2-pyrazinyl)urea; and N-{2-[bis(2-methoxyethyl)amino]-5-cyanophenyl}-N'-(5-cyano-2-pyrazinyl)urea.

7. The compound of claim 4 wherein one of $R^8$ and $R^9$ is arylalkyl and the other is selected from the group consisting of alkyl and hydroxyalkyl.

8. The compound of claim 7 selected from the group consisting of

N-{2-[benzyl(2-hydroxyethyl)amino]-5-bromophenyl)}-N'-(5-cyano-2-pyrazinyl)urea;

N-{5-bromo-2-[(2-hydroxy-2-phenylethyl)(methyl)amino]phenyl}-N'-(5-cyano-2-pyrazinyl)urea;

N-{2-[benzyl(2-hydroxyethyl)amino]-5-chlorophenyl}-N'-(5-cyano-2-pyrazinyl)urea;

N-{5-chloro-2-[(2-hydroxy-2-phenylethyl)(methyl)amino]phenyl}-N'-(5-cyano-2-pyrazinyl)urea; and N-{5-cyano-2-[(2-hydroxy-2-phenylethyl)(methyl)amino]phenyl}-N'-(5-cyano-2-pyrazinyl)urea.

9. The compound of claim 1 wherein $R^4$ is —(CHR$^6$)$_m$OR$^7$.

10. The compound of claim 9 wherein m is 0.

11. The compound of claim 10 wherein $R^7$ is selected from the group consisting of alkoxyalkyl and alkylsulfanylalkyl.

12. The compound of claim 11 selected from the group consisting of

N-[5-chloro-2-(2-methoxy-1-methylethoxy)phenyl]-N'-(5-cyano-2-pyrazinyl)urea;

N-[5-chloro-2-(2-ethoxy-1-methylethoxy)phenyl]-N'-(5-cyano-2-pyrazinyl)urea;

N-[5-chloro-2-(2-methoxyethoxy)phenyl]-N'-(5-cyano-2-pyrazinyl)urea;

N-[5-chloro-2-(2-isopropoxyethoxy)phenyl]-N'-(5-cyano-2-pyrazinyl)urea;

N-[5-chloro-2-(2-ethoxyethoxy)phenyl]-N'-(5-cyano-2-pyrazinyl)urea;

N-{5-chloro-2-[2-(methylsulfanyl)ethoxy]phenyl}-N'-(5-cyano-2-pyrazinyl)urea; and N-[5-chloro-2-(3-methoxy-3-methylbutoxy)phenyl]-N'-(5-cyano-2-pyrazinyl)urea.

13. The compound of claim 10 wherein $R^7$ is (cycloalkyl)alkyl.

14. The compound of claim 13 selected from the group consisting of

N-{5-chloro-2-[(2-methylcyclopropyl)methoxy]phenyl}-N'-(5-cyano-2-pyrazinyl)urea;

N-[5-chloro-2-(cyclopropylmethoxy)phenyl]-N'-(5-cyano-2-pyrazinyl)urea;

N-{5-chloro-2-[(1-methylcyclopropyl)methoxy]phenyl}-N'-(5-cyano-2-pyrazinyl)urea;

N-[5-chloro-2-(2-cyclohexylethoxy)phenyl]-N'-(5-cyano-2-pyrazinyl)urea;

N-{2-[(1S,4S)-bicyclo[2.2.1]hept-2-ylmethoxy]-5-chlorophenyl}-N'-(5-cyano-2-pyrazinyl)urea; and ethyl 2-{[4-chloro-2-({[(5-cyano-2-pyrazinyl)amino]carbonyl}amino)phenoxy]methyl}cyclopropanecarboxylate.

15. The compound of claim 10 wherein $R^7$ is selected from the group consisting of alkenyl, alkoxyalkoxyalkyl, alkynyl, haloalkyl, and hydroxyalkyl.

16. The compound of claim 15 selected from the group consisting of

N-(5-chloro-2-{[(2S)-2,3-dihydroxypropyl]oxy}phenyl)-N'-(5-cyano-2-pyrazinyl)urea;

N-(5-chloro-2-{[(2R)-2,3-dihydroxypropyl]oxy}phenyl)-N'-(5-cyano-2-pyrazinyl)urea;

N-{5-chloro-2-[2-(2-methoxyethoxy)ethoxy]phenyl}-N'-(5-cyano-2-pyrazinyl)urea;

N-[2-(allyloxy)-5-chlorophenyl]-N'-(5-cyano-2-pyrazinyl)urea;

N-{5-chloro-2-[(3-methyl-2-butenyl)oxy]phenyl}-N'-(5-cyano-2-pyrazinyl)urea;

N-[5-chloro-2-(3-pentynyloxy)phenyl]-N'-(5-cyano-2-pyrazinyl)urea; and

N-[5-chloro-2-(2-chloro-1-methoxyethoxy)phenyl]-N'-(5-cyano-2-pyrazinyl)urea.

17. The compound of claim 10 wherein $R^7$ is selected from the group consisting of alkoxycarbonylalkyl, arylcarbonylalkyl, aryloxyalkyl, cycloalkenyl, cycloalkyl, and heteroarylalkoxyalkyl.

18. The compound of claim 17 selected from the group consisting of

N-[5-chloro-2-(2-cyclohexen-1-yloxy)phenyl]-N'-(5-cyano-2-pyrazinyl)urea;

N-{2-[2-(4-bromophenoxy)ethoxy]-5-chlorophenyl}-N'-(5-cyano-2-pyrazinyl)urea;

N-(5-chloro-2-{2-[3-(6-methyl-2-pyridinyl)propoxy]ethoxy}phenyl)-N'-(5-cyano-2-pyrazinyl)urea;

N-[5-chloro-2-(2-oxo-2-phenylethoxy)phenyl]-N'-(5-cyano-2-pyrazinyl)urea;

N-[5-chloro-2-(3-cyclopenten-1-yloxy)phenyl]-N'-(5-cyano-2-pyrazinyl)urea;

N-(5-chloro-2-{[(3R,4S)-3,4-dihydroxycyclopentyl]oxy}phenyl)-N'-(5-cyano-2-pyrazinyl)urea;

N-(5-chloro-2-{[(1S,3R)-3-hydroxycyclopentyl]oxy}phenyl)-N'-(5-cyano-2-pyrazinyl)urea; and ethyl 6-[4-chloro-2-({[(5-cyano-2-pyrazinyl)amino]carbonyl}amino)phenoxy]hexanoate.

19. The compound of claim 1 wherein

X is —N—;

$R^1$ is cyano;

$R^2$ is selected from the group consisting of cyano and halo; and $R^3$ is hydrogen.

20. A pharmaceutical composition comprising a compound of claim 1 or a therapeutically acceptable salt thereof, in combination with a therapeutically acceptable carrier.

* * * * *